US012403311B2

(12) United States Patent
Humayun et al.

(10) Patent No.: US 12,403,311 B2
(45) Date of Patent: Sep. 2, 2025

(54) SYSTEM AND METHOD TO INDUCE EPIGENETIC CHANGES TO THE CELLS AND TISSUE OF THE EYE AND ORBIT

(71) Applicant: UNIVERSITY OF SOUTHERN CALIFORNIA, Los Angeles, CA (US)

(72) Inventors: Mark S. Humayun, Los Angeles, CA (US); Gianluca Lazzi, Los Angeles, CA (US); Bodour Salhia, Los Angeles, CA (US); Manjunath Machnoor, Los Angeles, CA (US); Javad Paknahad, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/766,600

(22) PCT Filed: Oct. 28, 2020

(86) PCT No.: PCT/US2020/057680
§ 371 (c)(1),
(2) Date: Apr. 5, 2022

(87) PCT Pub. No.: WO2021/086924
PCT Pub. Date: May 6, 2021

(65) Prior Publication Data
US 2024/0100334 A1    Mar. 28, 2024

Related U.S. Application Data

(60) Provisional application No. 62/927,038, filed on Oct. 28, 2019.

(51) Int. Cl.
*A61N 1/36* (2006.01)
*A61N 1/04* (2006.01)
(Continued)

(52) U.S. Cl.
CPC ....... *A61N 1/36046* (2013.01); *A61N 1/0476* (2013.01); *A61N 1/36014* (2013.01);
(Continued)

(58) Field of Classification Search
CPC .............. A61N 1/3787; A61N 1/37229; A61N 1/36014; A61N 1/36046
See application file for complete search history.

(56) References Cited

U.S. PATENT DOCUMENTS 4,628,933 A * 12/1986 Michelson ........... A61N 1/0543
607/61
5,935,155 A * 8/1999 Humayun ........... A61N 1/36046
607/54
(Continued)

FOREIGN PATENT DOCUMENTS

WO    2000056393 A1    9/2000
WO    2017048731 A1    3/2017
(Continued)

OTHER PUBLICATIONS

International Search Report and Written Opinion (mailing date Feb. 10, 2021) for Corresponding International PCT Patent Application No. PCT/US2020/057680, filed Oct. 28, 2020.
(Continued)

*Primary Examiner* — Eric D. Bertram

(57) ABSTRACT

Methods, systems, and apparatus for causing changes to cells or tissue within or adjacent to an eye. The system includes an external RF coil configured to transmit RF signals. The system also includes a wearable device configured to be removably disposed on the eye, the wearable device including a plurality of internal radiofrequency (RF) coils configured to receive the RF signals from the external RF coil and a plurality of stimulating electrodes configured to electromagnetically stimulate a portion of the eye or an
(Continued)

area adjacent to the eye, causing changes to cells or tissue within or adjacent to the eye.

20 Claims, 22 Drawing Sheets

(51) Int. Cl.
A61N 1/40 (2006.01)
C12Q 1/6874 (2018.01)
C12Q 1/6883 (2018.01)

(52) U.S. Cl.
CPC .............. A61N 1/40 (2013.01); C12Q 1/6874 (2013.01); C12Q 1/6883 (2013.01); C12Q 2600/106 (2013.01); C12Q 2600/154 (2013.01)

(56) References Cited

U.S. PATENT DOCUMENTS

| | | | |
|---|---|---|---|
| 9,687,652 B2 | 6/2017 | Franke et al. | |
| 10,117,740 B1* | 11/2018 | Lee | G02C 7/083 |
| 2002/0095193 A1* | 7/2002 | Ok | A61F 2/14 607/54 |
| 2006/0271129 A1 | 11/2006 | Tai et al. | |
| 2007/0244523 A1* | 10/2007 | Grill | A61N 1/0543 607/54 |
| 2008/0183242 A1* | 7/2008 | Tano | A61N 1/36046 607/53 |
| 2010/0305659 A1* | 12/2010 | Grill | A61N 1/36046 607/54 |
| 2011/0184271 A1 | 7/2011 | Veciana et al. | |
| 2012/0130398 A1 | 5/2012 | Ackermann et al. | |
| 2014/0058506 A1 | 2/2014 | Tai et al. | |
| 2016/0106576 A1 | 4/2016 | Badawi et al. | |
| 2017/0316487 A1* | 11/2017 | Mazed | G06Q 30/0241 |
| 2018/0104475 A1* | 4/2018 | Ho | A61N 1/3787 |
| 2018/0316224 A1* | 11/2018 | Maynard | G02C 7/044 |
| 2018/0332409 A1 | 11/2018 | Cahan et al. | |
| 2019/0344076 A1* | 11/2019 | Irazoqui | G02C 7/04 |
| 2019/0369044 A1* | 12/2019 | Chang | G01N 27/4146 |
| 2019/0381324 A1* | 12/2019 | Wang | A61N 1/36007 |
| 2020/0030615 A1* | 1/2020 | Loudin | B29D 11/00038 |
| 2020/0101290 A1* | 4/2020 | Rockley | A61N 1/36014 |
| 2022/0280777 A1* | 9/2022 | Humayun | A61N 1/0543 |

FOREIGN PATENT DOCUMENTS

| | | |
|---|---|---|
| WO | WO2017-167670 | 10/2017 |
| WO | 2019028474 A1 | 2/2019 |

OTHER PUBLICATIONS

Extended European Search Report and Written Opinion (dated Oct. 16, 2023) for Corresponding European Patent Application EP20881237.

* cited by examiner

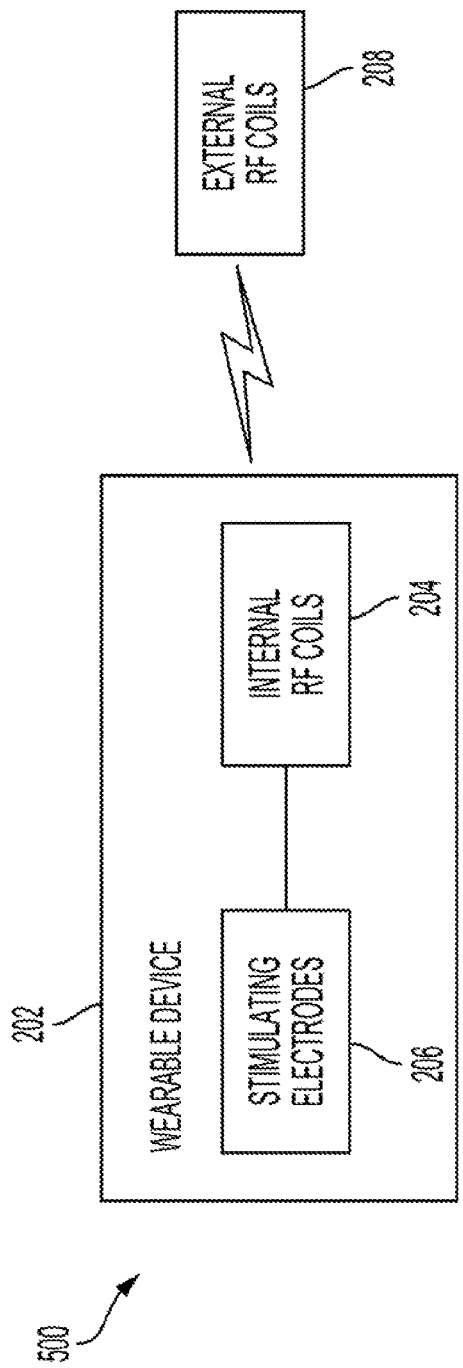
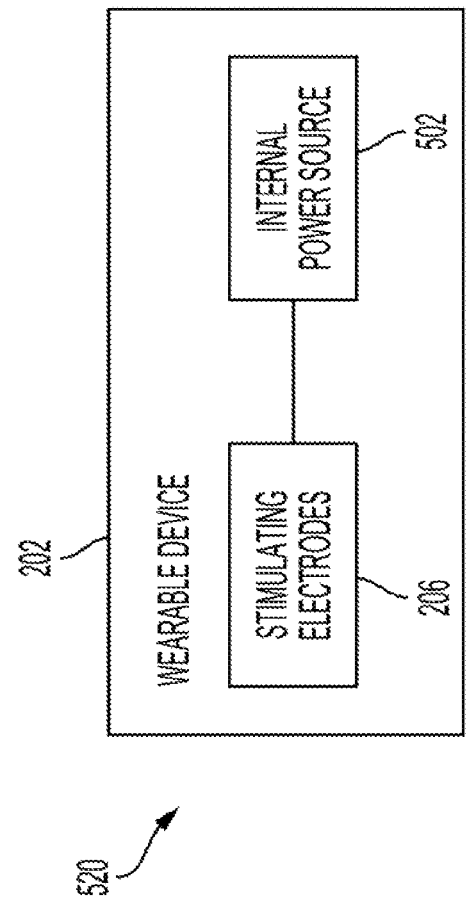

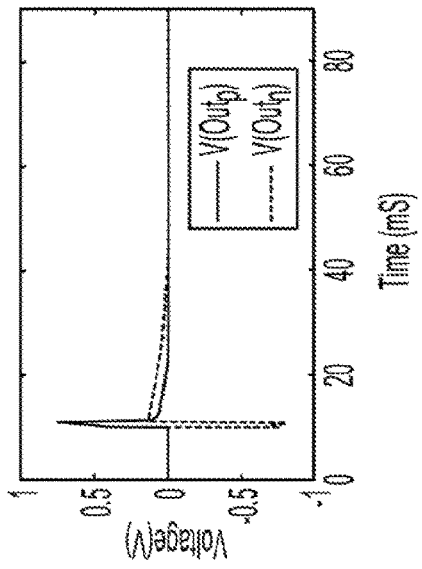
FIG. 7E
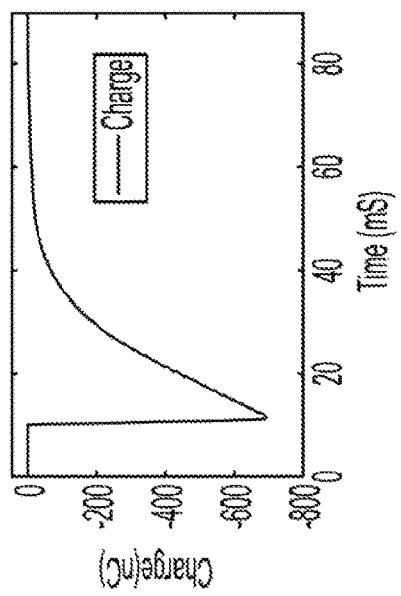
FIG. 7B
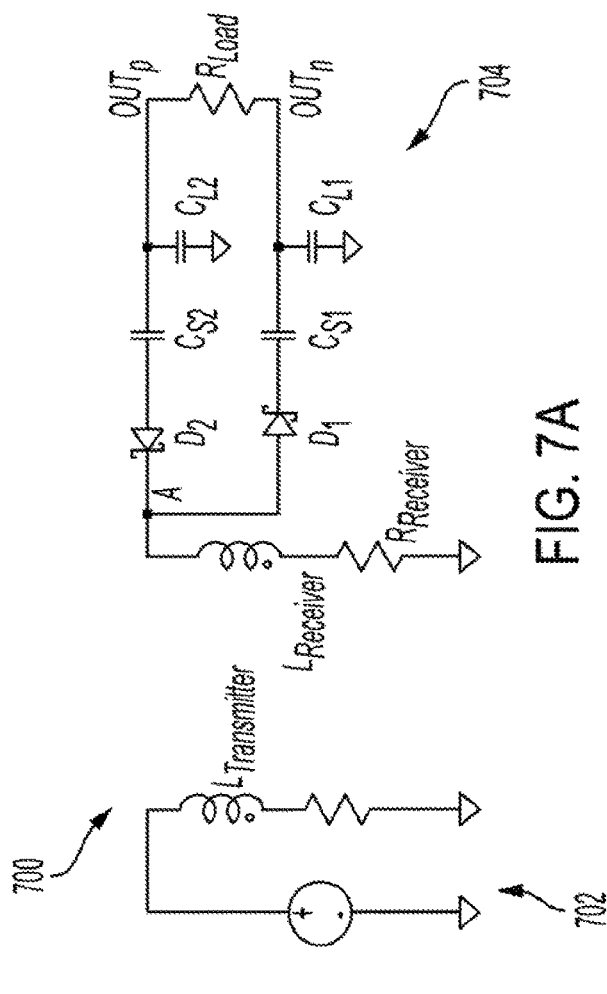
FIG. 7A
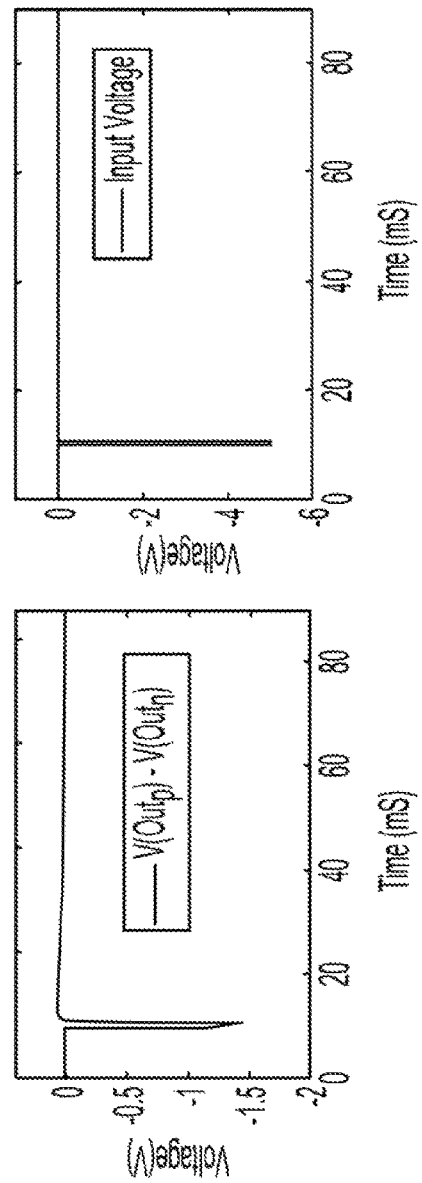
FIG. 7D
FIG. 7C

| seqnames | start | end | widthC | Gcounts | value | p.MWU | p.2D.KS |
|---|---|---|---|---|---|---|---|
| chr5 | 116507391 | 116507633 | 243 | 23 | 0.21 | 8.1E09 | 5.1E08 |
| chr3 | 154043557 | 154043745 | 189 | 10 | 0.0021 | 9.3E10 | 5.1E10 |
| chr5 | 169587874 | 169588155 | 282 | 12 | 1 | 0.00000046 | 0.000041 |
| chr8 | 99927798 | 99928011 | 214 | 10 | 1 | 0.0000021 | 0.000023 |
| chr10 | 106290494 | 106290897 | 404 | 12 | 1 | 0.000024 | 0.00095 |
| chr19 | 44996356 | 44996833 | 478 | 13 | 1 | 0.00000039 | 0.0000022 |
| chr4 | 79826397 | 79826661 | 265 | 10 | 1 | 0.00000068 | 0.00004 |
| chr1 | 264774195 | 264774394 | 200 | 10 | 1 | 0.00000029 | 0.000036 |
| chrX | 20317293 | 20317453 | 161 | 10 | 1 | 0.00000073 | 0.0000065 |
| chr18 | 26730603 | 26730813 | 211 | 10 | 1 | 0.000074 | 0.0002 |
| chrX | 140878404 | 140878549 | 146 | 14 | 0.0089 | 4.1E11 | 2.1E09 |
| chr18 | 28437140 | 28437488 | 349 | 10 | 1 | 0.000012 | 0.00083 |
| chr3 | 164385337 | 164385609 | 273 | 10 | 1 | 0.0000046 | 0.000023 |
| chr5 | 5989025 | 5989304 | 280 | 16 | 1 | 6.8E10 | 0.0000015 |
| chr14 | 79791373 | 79791901 | 529 | 10 | 1 | 0.000007 | 0.00011 |
| chr12 | 44350872 | 44351052 | 181 | 10 | 1 | 0.0000086 | 0.00012 |
| chr1 | 250858376 | 250858735 | 360 | 10 | 1 | 0.00000079 | 0.00095 |
| chr5 | 49321956 | 49322393 | 438 | 10 | 1 | 0.00025 | 0.000015 |
| chr1 | 80273940 | 80274196 | 257 | 10 | 1 | 0.00000085 | 0.0000038 |
| chr6 | 109960645 | 109960871 | 227 | 10 | 1 | 0.000024 | 0.00058 |
| chr12 | 15277546 | 15277883 | 338 | 10 | 1 | 0.000021 | 0.00012 |
| chrX | 62373885 | 62374034 | 150 | 10 | 1 | 0.00011 | 0.00095 |
| chr19 | 17196993 | 17197394 | 402 | 10 | 1 | 0.000007 | 0.0015 |
| chrX | 14265824 | 14266678 | 855 | 10 | 1 | 0.0012 | 0.038 |
| chr5 | 116660463 | 116660681 | 219 | 10 | 1 | 0.0000043 | 0.000023 |
| chrX | 72515021 | 72515348 | 328 | 33 | 0.023 | 5.3E43 | 5.5E09 |
| chr9 | 54332355 | 54332598 | 244 | 29 | 0.18 | 4.5E42 | 4.3E08 |
| chr1 | 79864753 | 79865073 | 321 | 35 | 0.37 | 5.8E40 | 8.9E08 |
| chr8 | 116307194 | 116307410 | 217 | 26 | 0.000092 | 4.2E42 | 2.2E11 |
| chr9 | 30161632 | 30161701 | 70 | 12 | 0.0029 | 3.8E40 | 6.9E10 |
| chrX | 106823881 | 106824214 | 334 | 15 | 0.000012 | 1.9E11 | 3E42 |
| chrX | 27015408 | 27015617 | 210 | 17 | 0.0094 | 7.4E42 | 2.2E09 |
| chr12 | 14563429 | 14563648 | 220 | 10 | 1 | 0.00011 | 0.00056 |
| chr15 | 38386748 | 38387001 | 254 | 10 | 1 | 0.000016 | 0.00094 |
| chr12 | 51243890 | 51244134 | 245 | 10 | 1 | 0.00000043 | 0.000069 |
| chr1 | 70210955 | 70211091 | 137 | 10 | 1 | 1.8E08 | 0.00000051 |
| chr12 | 17775097 | 17775262 | 166 | 15 | 0.038 | 1.4E42 | 9E09 |
| chr1 | 277905765 | 277906212 | 448 | 10 | 1 | 8.7E08 | 0.0000018 |
| chr8 | 70551495 | 70551540 | 46 | 12 | 1 | 0.0000096 | 0.00001 |
| chr19 | 54120764 | 54120962 | 199 | 10 | 1 | 0.00019 | 0.00057 |
| chr18 | 59942834 | 59943045 | 212 | 10 | 1 | 0.0000057 | 0.00021 |
| chrX | 77262947 | 77263229 | 283 | 22 | 1 | 1.2E09 | 0.0000081 |
| chrX | 109940020 | 109940231 | 212 | 20 | 1 | 0.0000026 | 0.00042 |

FIG. 13A

| nearest_gene | distance | dmrvalue | mean.covg.all | onPromoter | onExon1 | onBody | onCpGIsland |
|---|---|---|---|---|---|---|---|
| Nfia | 0 | 0.41679798 | 5.086956522 | FALSE | FALSE | TRUE | FALSE |
| Nnat | 126 | 0.40287398 | 5.866666667 | TRUE | FALSE | FALSE | FALSE |
| Kcnab2 | 0 | 0.39976471 | 5.430555556 | FALSE | FALSE | TRUE | FALSE |
| Plscr4 | 10064 | 0.37490741 | 5.516666667 | FALSE | FALSE | FALSE | FALSE |
| Sept9 | 0 | 0.35604858 | 6.069444444 | FALSE | FALSE | TRUE | FALSE |
| Cntnap4 | 0 | 0.34393847 | 6 | FALSE | FALSE | TRUE | FALSE |
| Mpp6 | 19843 | 0.33153078 | 6.833333333 | FALSE | FALSE | FALSE | FALSE |
| Lzts2 | 0 | 0.33148981 | 7.4 | TRUE | FALSE | TRUE | FALSE |
| Wnk3 | 0 | 0.32799756 | 5.716666667 | FALSE | FALSE | TRUE | FALSE |
| Epb4l4a | 0 | 0.32065888 | 6.35 | FALSE | FALSE | TRUE | FALSE |
| Zic3 | 0 | 0.31492819 | 5.761904762 | TRUE | TRUE | TRUE | TRUE |
| Mzb1 | 0 | 0.31447996 | 6.483333333 | FALSE | FALSE | TRUE | FALSE |
| Tmem189 | 0 | 0.311169432 | 6.216666667 | FALSE | FALSE | TRUE | FALSE |
| Slco5a1 | 0 | 0.30806878 | 6.03125 | FALSE | FALSE | TRUE | FALSE |
| Sorcs2 | 0 | 0.30654762 | 6.616666667 | FALSE | FALSE | TRUE | FALSE |
| Nos1 | 0 | 0.30459476 | 6.05 | FALSE | FALSE | TRUE | FALSE |
| Sgms1 | 0 | 0.29974479 | 7.016666667 | FALSE | FALSE | TRUE | FALSE |
| Chr1 | 0 | 0.29927249 | 7.133333333 | FALSE | FALSE | TRUE | FALSE |
| Ppp1r13l | 0 | 0.29887566 | 6.833333333 | FALSE | TRUE | TRUE | FALSE |
| Ift43 | 0 | 0.29649952 | 6.366666667 | FALSE | FALSE | TRUE | FALSE |
| Sdk1 | 0 | 0.29204666 | 6.466666667 | FALSE | FALSE | TRUE | FALSE |
| Arx | 0 | 0.26396825 | 5.183333333 | FALSE | FALSE | TRUE | TRUE |
| Rpgrip1l | 0 | 0.25708754 | 6.533333333 | FALSE | FALSE | TRUE | FALSE |
| Rpgr | 4332 | 0.25203704 | 5.816666667 | FALSE | FALSE | FALSE | FALSE |
| Nfia | 0 | 0.213305824 | 6.666666667 | FALSE | FALSE | TRUE | FALSE |
| Phka1 | 0 | 0.1850008 | 5.580808081 | FALSE | FALSE | TRUE | TRUE |
| Stat1 | 4396 | -0.4090393 | 2.350574713 | FALSE | FALSE | FALSE | FALSE |
| Nova2 | 0 | -0.1288738 | 5.533333333 | FALSE | FALSE | TRUE | TRUE |
| Rassf1 | 0 | -0.1516086 | 5.782051282 | FALSE | TRUE | FALSE | TRUE |
| Smap1 | 0 | -0.1650172 | 8.375 | FALSE | FALSE | TRUE | FALSE |
| Bex3 | 0 | 0.58410663 | 3.066666667 | TRUE | TRUE | TRUE | TRUE |
| Msl3 | 207 | -0.2667056 | 5.921568627 | TRUE | FALSE | FALSE | TRUE |
| Sdk1 | 0 | -0.3015536 | 5.183333333 | FALSE | FALSE | TRUE | FALSE |
| Fgf9 | 0 | -0.3309752 | 5.433333333 | FALSE | FALSE | TRUE | FALSE |
| Mn1 | 0 | -0.3542136 | 6.1 | FALSE | FALSE | TRUE | FALSE |
| Peg3 | 0 | -0.3945238 | 5.133333333 | FALSE | TRUE | TRUE | TRUE |
| Pdgfa | 18910 | -0.4050152 | 5.5 | FALSE | FALSE | FALSE | FALSE |
| Ablim1 | 0 | -0.4124964 | 5.733333333 | FALSE | FALSE | TRUE | FALSE |
| Dpp8 | 0 | 0.25167148 | 5.277777778 | FALSE | FALSE | TRUE | FALSE |
| Gse1 | 0 | 0.23461159 | 5.5 | FALSE | FALSE | TRUE | FALSE |
| Fech | 0 | 0.22750786 | 6.45 | FALSE | TRUE | FALSE | FALSE |
| Pgk1 | 168 | 0.22521304 | 6.712121212 | TRUE | FALSE | FALSE | TRUE |
| Nrk | 206 | 0.20930556 | 5.241666667 | TRUE | FALSE | FALSE | TRUE |

FROM FIG. 13A        FIG. 13B

SYSTEM AND METHOD TO INDUCE EPIGENETIC CHANGES TO THE CELLS AND TISSUE OF THE EYE AND ORBIT

CROSS REFERENCE TO RELATED APPLICATIONS

This application claims the benefit and priority of U.S. Provisional Application Ser. No. 62/927,038, filed Oct. 28, 2019, entitled "System and Method To Induce Epigenetic Changes To The Cells and Tissue Of The Eye and Orbit," the contents of which are herein incorporated by reference in its entirety.

GOVERNMENT LICENSE RIGHTS

This invention was made with United States government support under Contract No. 1933394 awarded by the National Science Foundation. The United States government has certain rights in this invention.

BACKGROUND

1. Field

This specification relates to systems and methods for inducing changes to an eye or adjacent areas.

2. Description of the Related Art

Retinal blindness, such as Retinitis Pigmentosa (RP), Age-Related Macular Degeneration (AMD), and glaucoma (POAG) are multi-phase conditions characterized by unrelenting neuronal death (photoreceptor loss in RP and AMD and ganglion cell loss in POAG). Neuronal rewiring, reprogramming, and migration can manifest early in these conditions. A number of mechanisms have been identified as to why neuronal death occurs in these different retinal blinding disorders (e.g., genetic mutations in RP, lipid metabolism abnormalities and inflammation in AMD, and elevated intraocular pressure in POAG to name a few). Although treatments to ameliorate these conditions exist, for many afflicted, there is no cure. Thus, there is a need for improved treatment of these conditions.

SUMMARY

What is described is a system for causing changes to cells or tissue within or adjacent to an eye. The system includes an external RF coil configured to transmit RF signals. The system also includes a wearable device configured to be removably disposed on the eye, the wearable device including a plurality of internal radiofrequency (RF) coils configured to receive the RF signals from the external RF coil and a plurality of stimulating electrodes configured to electromagnetically stimulate a portion of the eye or an area adjacent to the eye, causing changes to cells or tissue within the eye or adjacent to the eye.

Also described is a method for causing changes to cells or tissue within or adjacent to an eye. The method includes transmitting, by an external RF coil, RF signals. The method also includes receiving, by a plurality of internal radiofrequency (RF) coils of a wearable device removably disposed on the eye, the RF signals from the external RF coil. The method also includes stimulating, by a plurality of stimulating electrodes, a portion of the eye or an area adjacent to the eye, causing the changes to the cells or tissue within or adjacent to the eye.

Also described is a wearable device having an outer surface and an inner surface, the inner surface configured to removably contact an eye of a user. The wearable device also includes a plurality of stimulating electrodes configured to electromagnetically stimulate a portion of the eye or an area adjacent to the eye, causing changes to cells or tissue within or adjacent to the eye.

BRIEF DESCRIPTION OF THE DRAWINGS

Other systems, methods, features, and advantages of the present invention will be apparent to one skilled in the art upon examination of the following figures and detailed description. Component parts shown in the drawings are not necessarily to scale, and may be exaggerated to better illustrate the important features of the present invention.

FIGS. 5A-5C illustrate embodiments of the system, according to various embodiments of the invention.

FIGS. 7A-7L illustrate a circuit schematic of the system and characteristics of these components, according to various embodiments of the invention.

FIGS. 13A-13B illustrate differentially methylated regions (DMRs) identified as being most significantly altered after electrical stimulation, according to embodiments of the invention.

DETAILED DESCRIPTION

Although the field of classical epigenetics has been widely studied, neuroepigenetics (pertaining to the study of epigenetics in post-mitotic neurons) is a relatively nascent and emerging field of study. Moreover, there is especially a lack of data on the epigenetics of the retina, which is considered an outgrowth of the Central Nervous System (CNS). Electrical stimulation of the retina or of cultured Muller cells may lead to transcriptomic changes that were indicative of neuroprotective changes, including downregulation of proapoptotic genes such as Bax and upregulation of prosurvival genes such as brain-derived neurotrophic factor (bdnf). The systems and methods described herein, for the first time, show that controlled non-invasive electrical stimulation can lead to epigenetic retinal changes with implications for neuroprotection. The systems and methods described herein allow for systematic, and therefore more reliable and reproducible, retinal neuroprotection.

Figure 1:
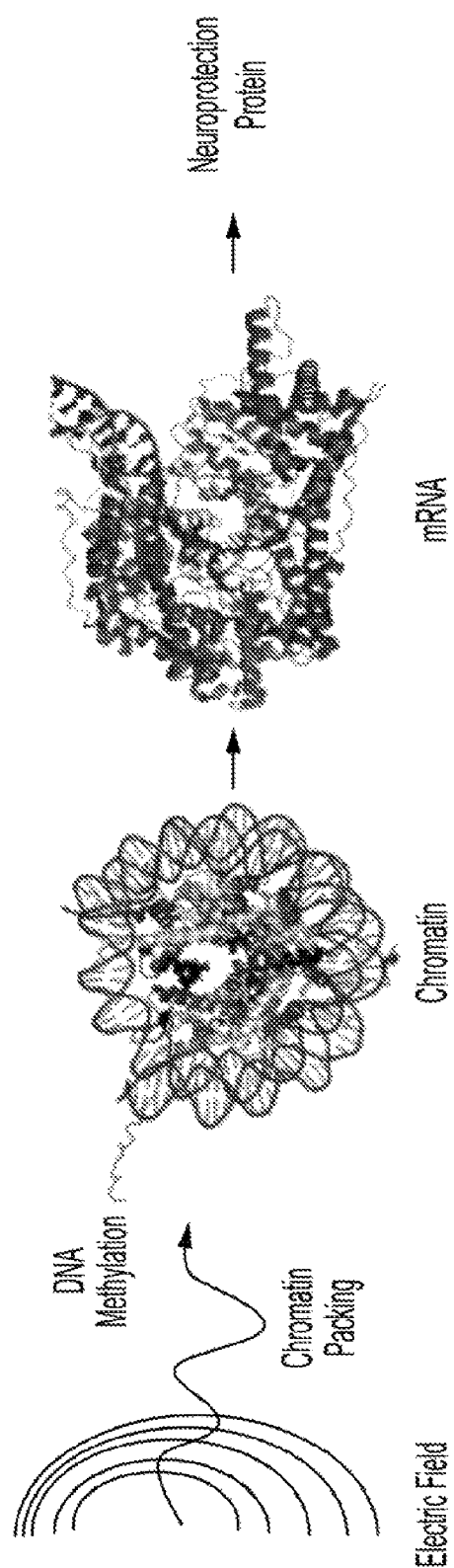
FIG. 1 illustrates an overview of a process of the system, according to various embodiments of the invention.

Accordingly, the systems and methods described herein are based on neuroepigenetic and chromatin remodeling of the retina induced through controlled electrical stimulation being a key molecular determinant of neuroprotection. This is pivotal for the treatment of retinal degenerative diseases, as shown in FIG. 1. The systems and methods described herein use a non-invasive wearable device to control electrical stimulation to induce epigenetic changes in the eye, thereby slowing the progression of neural degeneration. In some embodiments, the wearable device is a soft, doughnut shaped, contact lens with coils and electrodes worn at night time, which may be referred to herein as an "e-lens."

The pathological mechanisms in prevalent retinal disease (e.g., photoreceptor degeneration—such as Retinitis Pigmentosa (RP) and Age-Related Macular Degeneration (AMD)—or Primary Open Angle Glaucoma (POAG)) are becoming better understood. In spite of this, because of the more than 100 mutations that cause RP, for example, curing this family of mutations beyond the one-off gene therapy success as seen in the rare condition of Leber congenital amaurosis (RPE65 mutation) has been a daunting task. Similarly, intraocular pressure control becomes more difficult with the progression of glaucoma and neuroprotection is needed.

Previous uses of electrical and magnetic stimulation of the retina have been limited to rehabilitative devices, often utilized to bypass damaged neurons for partial vision restoration in patients with near total blindness. The systems and methods described herein introduce a different approach through a paradigm shift to prevent or delay neuronal loss experienced in incurable diseases such as RP, AMD, and POAG. Controlled electromagnetic fields can modulate functional and morphological neural alterations by exploiting transcriptional regulation of gene expression potentiated by chromatin packing and epigenomic remodeling. This approach may be used both early in the course of retinal diseases to slow down progression and late in the disease, complementing pharmacological and surgical therapies. It is important to note, that the form of electrical stimulation used herein is very different and not the type used in neural prosthetics which use electrical stimulation to bypass damaged photoreceptors and activate remaining retinal neurons to restore visual function.

Transcorneal electrical stimulation (TES) may reduce the rate of death of photoreceptors as well as delay the progression of retinal degenerative diseases. Other invasive methods may have a variety of effects on the retina, ranging from promotion of the survival of the axotomized retinal ganglion cells to rescue of photoreceptors. However, there is insufficient characterization of the causes responsible for these effects and limited understanding of the fundamental mechanisms.

Figure 2A:
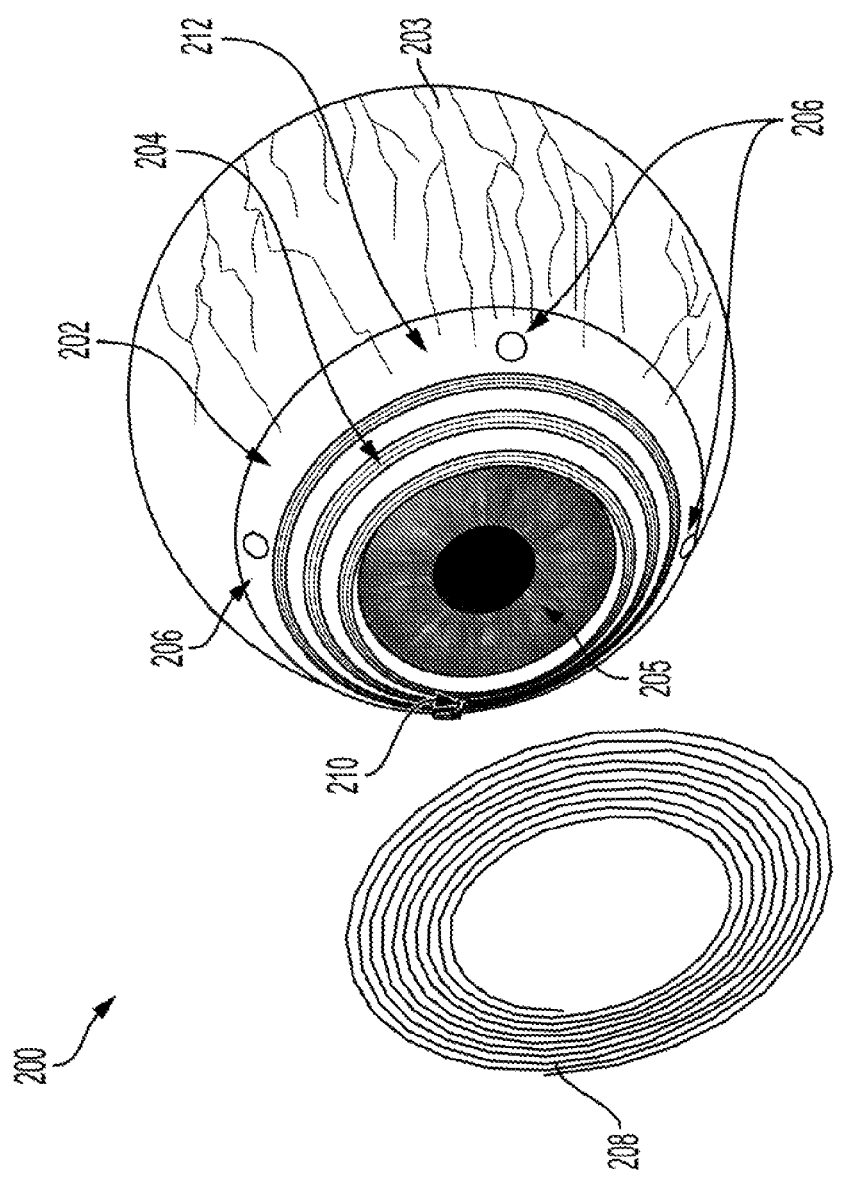
FIG. 2A illustrates a system for inducing changes to an eye or surrounding/adjacent areas, according to various embodiments of the invention.

FIG. 2A illustrates a system 200 for transcorneal electrical stimulation (TES). The system 200 includes a wearable device 202 configured to be removably disposed on an eye 203. That is, the wearable device 202 may be placed onto and removed from the eye 203. The wearable device 202 may be similar in material, shape, and dimensions, to a contact lens. In some embodiments, the wearable device 202 has an aperture 207 in the center, which allows for corneal oxygenation. The aperture 207 may also provide an opening for the cornea, iris, and pupil (among other portions of the eye 203) to enable the user to see through the wearable device 202.

The wearable device 202 includes a plurality of internal radiofrequency (RF) coils 204 connected to a plurality of stimulating electrodes 206. Also connected to the internal RF coils 204 and the stimulating electrodes may be one or more capacitors and diodes 210.

The stimulating electrodes 206 do not cover or damage the cornea and are designed so as to maximize electric current flow in the retina as determined through computational simulations described herein.

The internal RF coils 204 are configured to inductively receive power from external RF coils 208. That is, the external RF coils 208 send RF signals to the internal RF coils 204, and the internal RF coils 204 receive the RF signals. The power received from the external RF coils 208 is provided to the stimulating electrodes for stimulating various portions of the eye 203.

There may be any number of stimulating electrodes 206 located at various locations on the wearable device 202. The stimulating electrodes 206 may have any shape as may be appropriate for the treatment of the eye 203. There may also be any number of internal RF coils 204 each having any number of turns. The exact number of internal RF coils 204 and stimulating electrodes 206 may vary based on the application of the system 200 and/or the size or dimensions of the eye 203 of the user. Similarly, the exact number of external RF coils 208 may also vary.

Figure 2B:
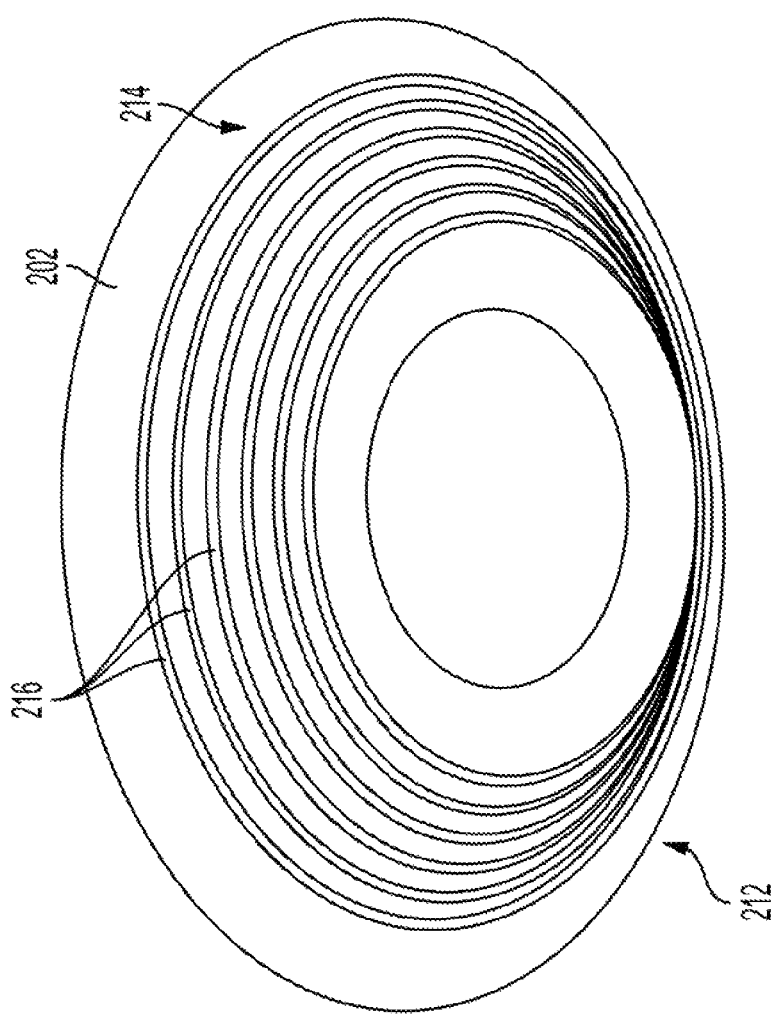
FIG. 2B illustrates a wearable device used in the system of FIG. 2A, according to various embodiments of the invention.

FIG. 2B illustrates the wearable device 202 without the internal RF coils 204. The wearable device 202 has an outer surface 212 and an inner surface 214. The inner surface 214 is configured to contact the eye 203 of the user. The outer surface 212 is opposite the inner surface 214 and the outer surface 212 faces the external RF coils 208. The wearable device 202 may also include a plurality of grooves 216 for receiving and housing the internal RF coils 204. The plurality of grooves 216 may be located on the outer surface 212 or the inner surface 214. In some embodiments, the plurality of grooves 216 are channels formed within the wearable device 202 and the internal RF coils 204 are embedded in the wearable device 202 between the outer surface 212 and the inner surface 214.

The stimulating electrodes 206 and the capacitors and diodes 210 may be located on the outer surface 212 or the inner surface 214 of the wearable device 202, or in some embodiments, may be embedded within the material of the wearable device 202 such that they are between the outer surface 212 and the inner surface 214. The stimulating electrodes 206 being effectively on the eye 203 helps to reduce impedance, as compared to a system where the stimulating electrodes are located outside of the eye and the eyelid is located between the eye and the stimulating electrodes. In systems where the eyelid separates the eye and the stimulating electrodes, the eyelid and other parts of the user may introduce impedance to the system, reducing efficiency and efficacy.

Figure 2C:
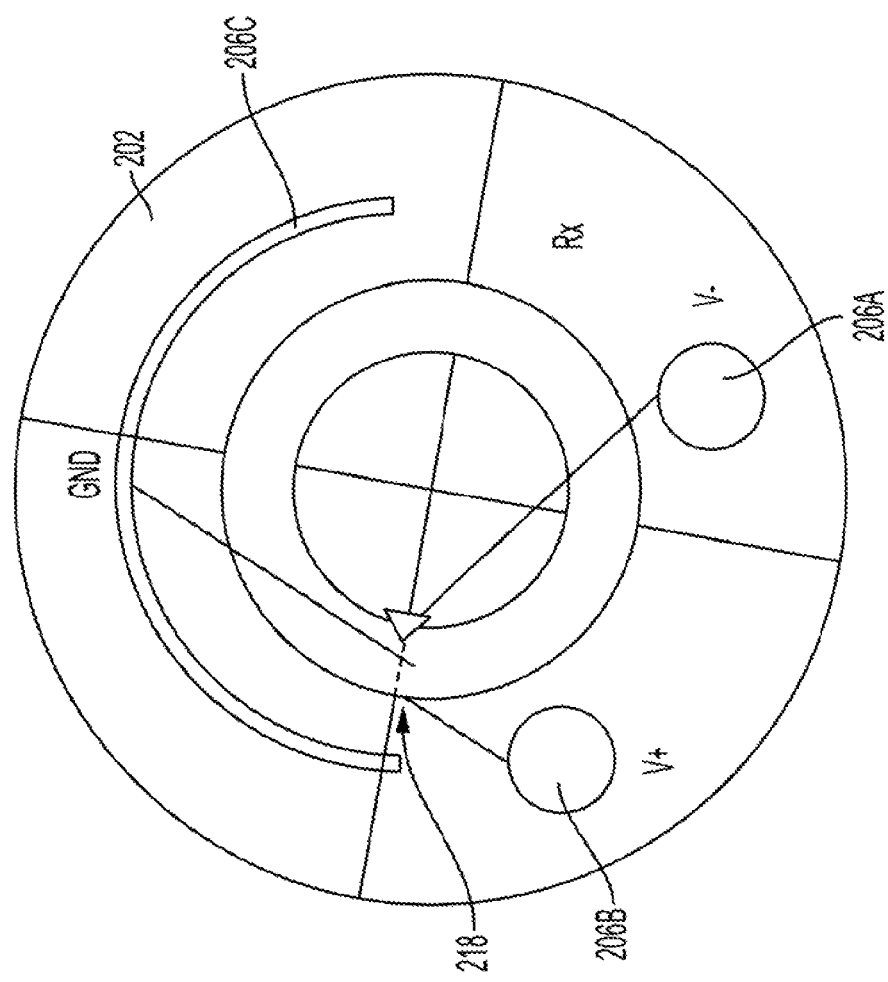
FIG. 2C illustrates the stimulating electrodes of the wearable device, according to various embodiments of the invention.

FIG. 2C illustrates an example layout of the stimulating electrodes 206 (e.g., negative electrode 206A, positive electrode 206B, ground electrode 206C) of the wearable device 202. There may be an arc-shaped ground electrode 206C located on an upper half of the wearable device 202. There may also be a negative electrode 206A located in a bottom right quadrant of the wearable device 202 and a positive electrode 206B located in a bottom left quadrant of the wearable device 202. The locations of the stimulating electrodes 206 may result in stimulation focused on a particular location 218 of the eye.

The embodiment shown in FIG. 2C is an example embodiment of locations and shapes of the stimulating electrodes 206 for focusing the stimulation at the location 218, and other embodiments for focusing the stimulation at other locations is possible.

There may be a link between changes in chromatin and epigenomic dynamics to electromagnetic field exposure, in particular as applied to the retina. While genetic and epigenetic alterations are involved in retinal degeneration initiation and progression, there are no epigenetic-based therapies to slow or halt the relentless progression of degenerative changes in the retina either at the photoreceptor or ganglion cell level. The systems and methods described herein are a completely different means of using electromagnetic fields and doing so non-invasively to induce epigenetic changes which would be neuroprotective (i.e., using a custom lens with biocompatible coils and electrodes to induce epigenetic changes to protect retinal neurons in animal models of photoreceptor and ganglion cell degeneration). Such an approach can be used both early in disease such as RP, AMD, and POAG or as an adjunct late in retinal diseases in combination with drugs, device or surgery. For example, the wearable device 202 could be worn overnight as it does not completely cover the cornea and hence does not interfere with corneal oxygenation. Overnight use would also make it easy to comply with as it would not interfere with daytime activities such as reading.

The systems and methods described herein could also be used for other neurodegenerative diseases and neural injuries such as stroke or closed head injury. Benefits of the systems and methods could also be realized to ailments where it is known that epigenetic alterations are involved in their progression, such as cancer. For example, early stage glioblastoma (type of brain cancer) could be slowed down in progression but also the neurons around the cancer could be protected from cell death.

Figure 3:
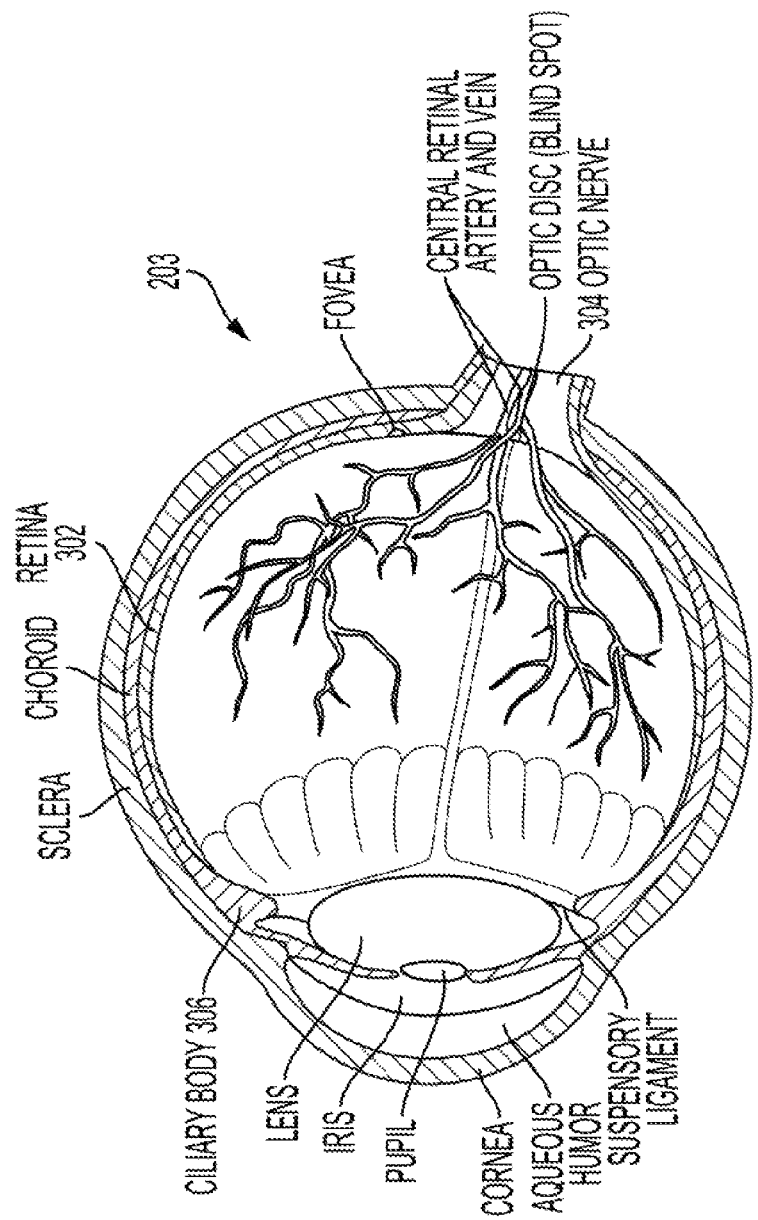
FIG. 3 illustrates parts of the eye that may be treated by the system, according to various embodiments of the invention.

FIG. 3 illustrates the eye 203 and various areas of the eye that may be stimulated using the system 200. In particular, the retina 302 and the optic nerve 304 may be stimulated to treat retinal blindness, such as Retinitis Pigmentosa (RP), Age-Related Macular Degeneration (AMD), and glaucoma (POAG). The ciliary body 306 may be stimulated to treat or delay presbyopia. Portions of the eye or within the eye may be treated, and areas adjacent to the eye may also be treated. The lacrimal gland (not pictured) which makes tears, may also be stimulated as a treatment for dry eye. The corneal epithelium may also be treated.

Figure 4:
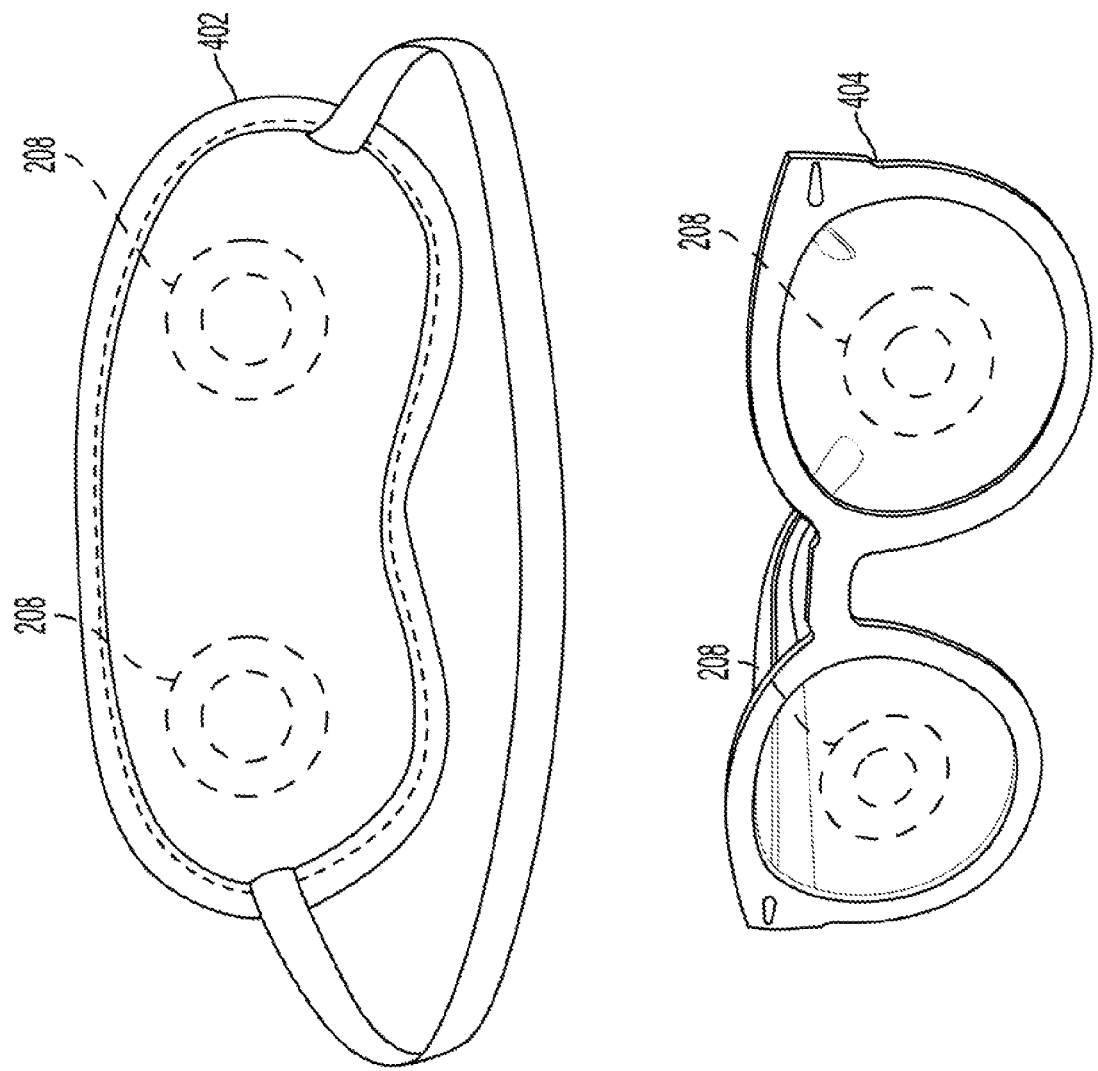
FIG. 4 illustrates external RF coils located on devices, according to various embodiments of the invention.

FIG. 4 illustrates example devices that can house the external RF coils 208. The external RF coils 208 may be housed in a mask 402 or glasses 404, for example. The system 200 may be used while the user is sleeping. Thus, a mask 402 with the RF coils 208 at a location corresponding to the eyes of the user may be used. Similarly, glasses 404 may be used when the user is not sleeping, with the RF coils 208 at a location corresponding to the eyes of the user. The RF coils 208 may be within sufficient distance to the internal RF coils 204 to inductively provide power to the stimulating electrodes 206 when the mask 402 or glasses 404 are worn by the user. The devices that house the external RF coils 208 may contain a power source or may be connected to a power source to provide current to the external RF coils 208.

FIG. 5A illustrates a system 500 having a wearable device 202 and external RF coils 208, as described herein. The wearable device 202 may have stimulating electrodes 206 connected to internal RF coils 204, also as described herein. The internal RF coils 204 may be inductively powered by the external RF coils 208. The internal RF coils 204 may power the stimulating electrodes 206 to stimulate portions of the eye, as described herein.

FIG. 5B illustrates a system 520 that does not include inductive power transfer. The wearable device 202 includes the stimulating electrodes 206 and also includes an internal power source 502 configured to provide power to the stimulating electrodes 206. The internal power source 502 may be disposed on or within the wearable device 202. In some embodiments, the internal power source 502 is a battery. In some embodiments, the internal power source 502 is a device that generates electricity based on movement, such as a triboelectric generator. The electricity may be generated based on movement of the user, including movement of the eye. In this way, the system 520 is a self-contained treatment apparatus. In embodiments where the internal power source 502 is a device that generates electricity, the internal power source 502 may also include a power storage device, such as a battery.

Figure 5C:
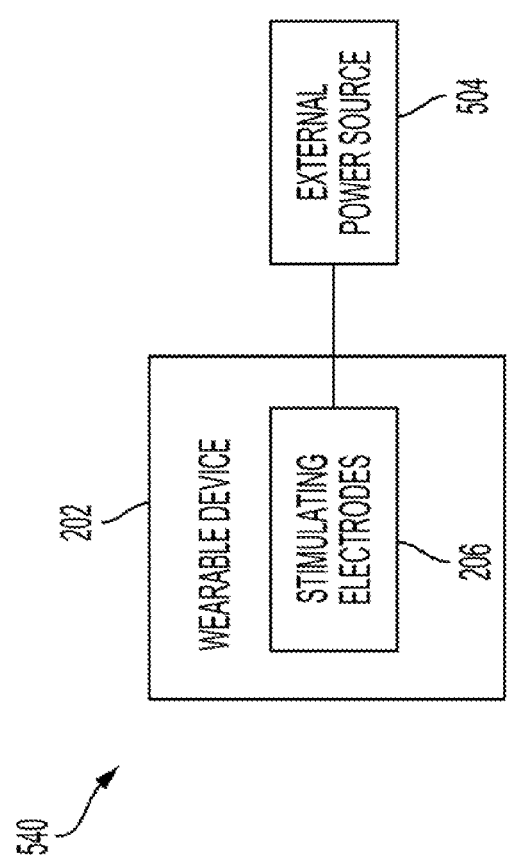

FIG. 5C illustrates a system 540 that also does not include inductive power transfer. The wearable device 202 includes the stimulating electrodes 206 that are connected to an external power source 504 configured to provide power to the stimulating electrodes 206. In some embodiments, the external power source 504 is a battery. In some embodiments, the external power source 504 is a device that generates electricity based on solar energy, such as a solar panel. In some embodiments, the external power source 504 is a device that generates electricity based on movement, such as a triboelectric generator. The electricity may be generated based on movement of the user. The external power source 504 may be located on a device to be worn by the user, such as glasses or a hat or an adhesive patch to be placed on the skin of the user. In embodiments where the external power source 504 is a device that generates electricity, the external power source 504 may also include a power storage device, such as a battery.

In some embodiments, an external mobile computing device, such as a smartphone, a laptop, or a tablet, may control the wearable device 202, including providing instructions for controlling the stimulating electrodes, for example. The external mobile computing device may be communicatively coupled to the wearable device 202 using a wired connection or a wireless connection, and communication may be performed using appropriate hardware, such as transceivers, and corresponding communications protocols, such as Bluetooth.

Figure 6A:
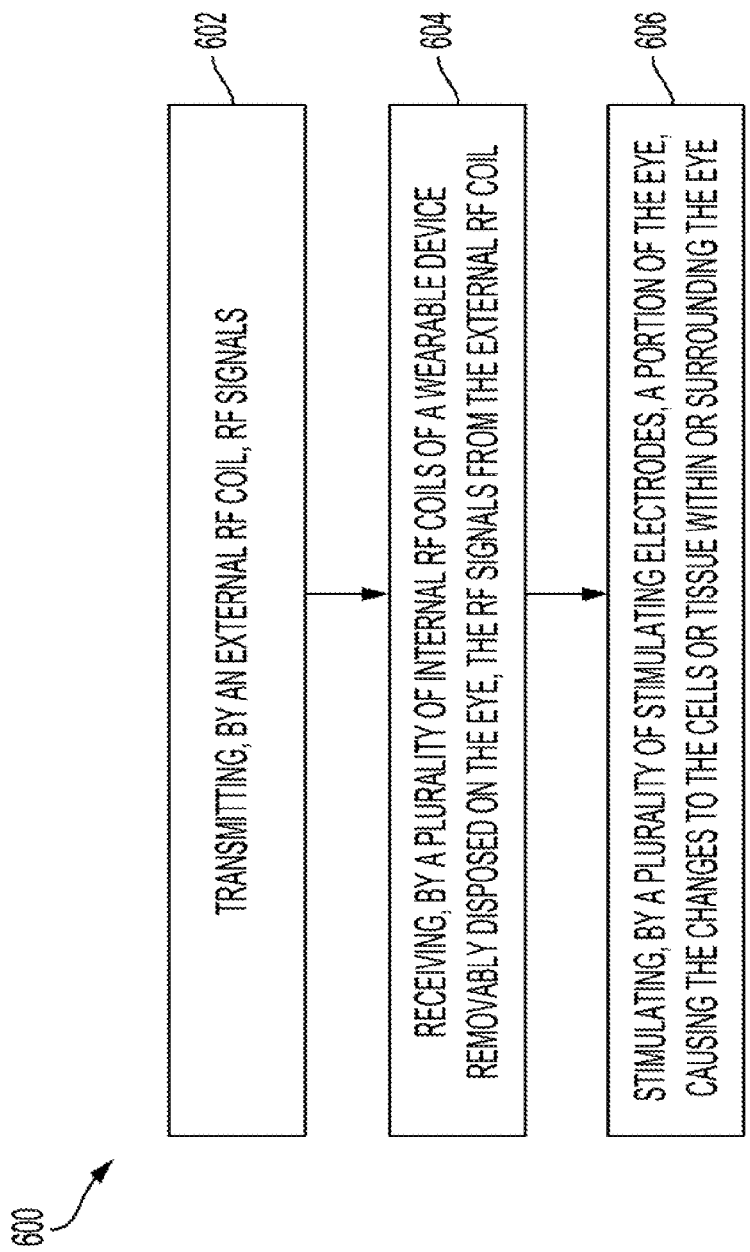
FIG. 6A illustrates a process of causing changes using the system, according to various embodiments of the invention.

FIG. 6A illustrates a process 600 for causing changes to cells or tissue within or adjacent to an eye. An external radiofrequency (RF) coil (e.g., external RF coils 208) transmits RF signals (step 602). A plurality of internal RF coils (e.g., internal RF coils 204) receive the RF signals from the external RF coil (step 604). The internal RF coils are located on a wearable device (e.g., wearable device 202) that is removably disposed on an eye (e.g., eye 203). A plurality of stimulating electrodes (e.g., stimulating electrodes 206) stimulate a portion of the eye or an area of the patient/user adjacent to the eye, causing changes to the cells or tissue within or adjacent to the eye (step 606). As used herein, "cells or tissue adjacent to the eye" refers to any cells or tissue near, around, in the vicinity of, adjacent to, or surrounding the eye and "area of the patient or user adjacent to the eye" refers to any area of the body near, around, in the vicinity of, adjacent to, or surrounding the eye.

Figure 6B:
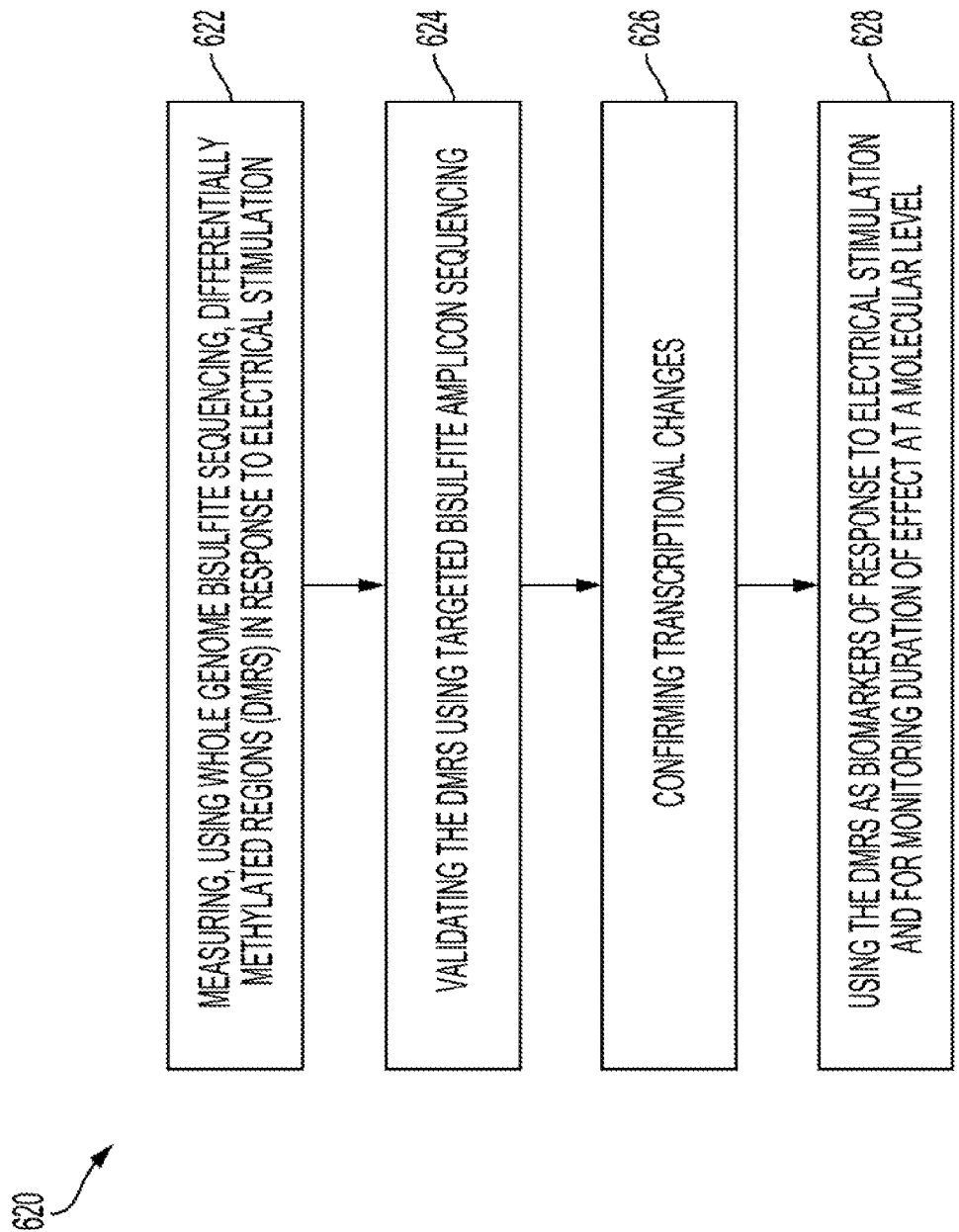
FIG. 6B illustrates a process of verifying inducement of epigenetic changes by the system, according to various embodiments of the invention.

FIG. 6B illustrates a process 620 for verifying inducement of epigenetic changes by the systems described herein. In particular, one or more steps of the process 600 may be performed using a computing device having a computer processor and a non-transitory memory storing instructions to be executed by the computer processor.

Differentially methylated regions (DMRs) are measured using whole genome bisulfate sequencing, in response to electrical stimulation (step 622). The DMRs are validated using targeted bisulfate amplicon sequencing (step 624). The transcriptional changes are confirmed (step 626) and the DMRs are used as biomarkers of response to electrical stimulation and for monitoring duration of effect at a molecular level (step 628).

With respect to the internal RF coils 204 and the external RF coils, various electrical components may be used. Conventionally, half-wave rectifiers are popular solutions for wireless passive electrodes. However, the half-wave rectifier (HWR) solution does not provide a charge-balanced waveform. That is, the HWR is always monophasic with each cycle. Use of charge-balanced waveforms are important to avoid imbalanced charge being transmitted through the eye tissue. Charge-balances waveforms are biphasic with each cycle.

Figure 7F:
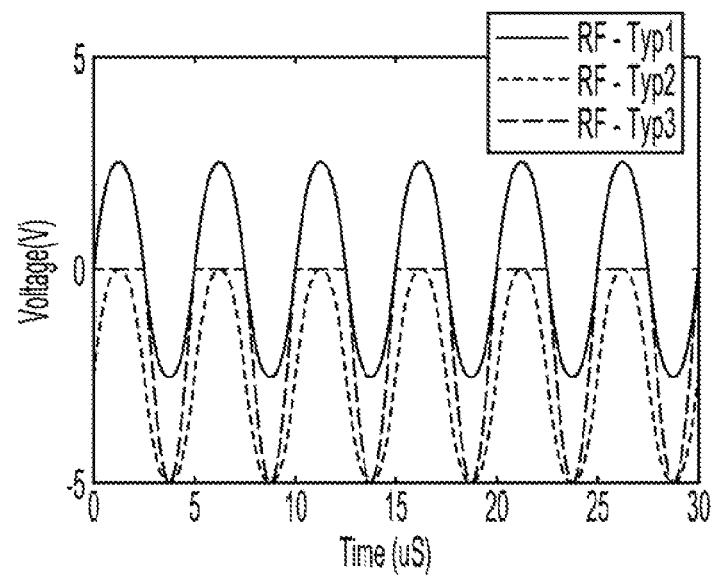
Figure 7G:
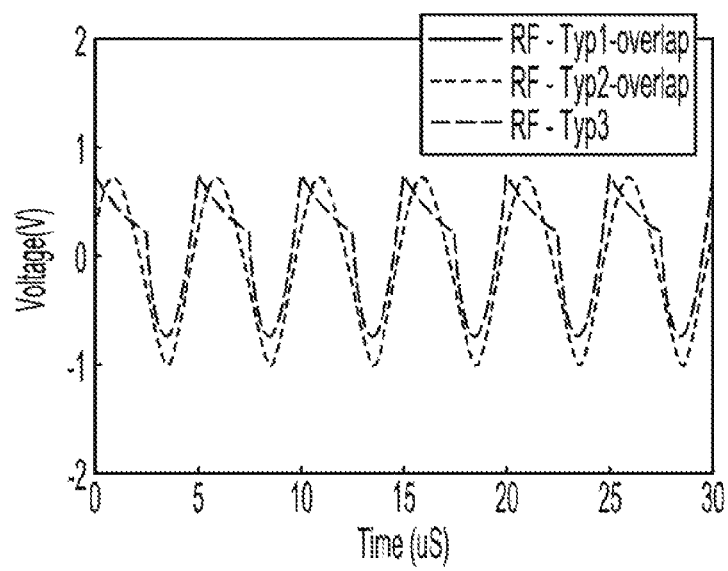

The circuit 700 shown in FIG. 7A may be used in the systems and methods described herein. The circuit 700 includes a transmitter portion 702 and a receiver portion 704. The transmitter portion 702 may be used with the external RF coils 206 and the receiver portion 704 may be used with the internal RF coils 204. The circuit 700 is capable of delivering a charge-balanced and higher output voltage than a half-wave rectifier system for a given load and input conditions. The output voltage across the load resistor is a difference of voltage across nodes $OUT_p$ and $OUT_n$. The circuit 700 assumes that the load of the current stimulating system is in kΩ. In an HWR circuit, one end of the load resistor is grounded, and the other end of the load resistor swings to either positive or negative value depending on the diode polarity. The load resistor's ground side is also connected to one end of the receiver coil to complete the circuit. However, unlike the HWR, the circuit 700 achieves higher voltage across the load resistor ($R_{load}$) by generating negative voltage without losing efficiency. The voltage across the load is given by V(a)-V(b).

The receiver inductor $L_{Receiver}$, $D_1$, $C_{s1}$ and $C_{L1}$ form an HWR charge-balanced positive rectifier circuit at the node $OUT_p$. Similarly, receiver inductor $L_{Receiver}$, $D_2$, $C_{s2}$, and $C_{L2}$ form an HWR charge-balanced negative rectifier circuit at the node $OUT_n$. Usually, a series capacitor in series with a single HWR circuit will reduce the output voltage. However, in the circuit 700, the effective output voltage increases when the load voltage is tapped differentially. The load resistor is connected such that it acts as an RF blocker. FIGS. 7B-7E illustrate performance of the circuit 700. The waveforms may be tuned by adjusting components, such as capacitors.

In addition, further steps may be performed to increase the output voltage further than what is provided by the circuit topology. The effects of these further steps are illustrated in FIGS. 7F-7I. The transmitted input signal may be a pulsed RF signal. Using a Type 3 RF signal not only leads to higher induced voltage, but also leads to asymmetric induction of the secondary coil open circuit voltage. This asymmetry in the induced voltage increases the load output voltage. The peak to peak voltages of all the signals may be the same (e.g., 5V). The asymmetry induced by the Type 3 signal can be attributed to differentiation property of the induction process.

Figure 7I:
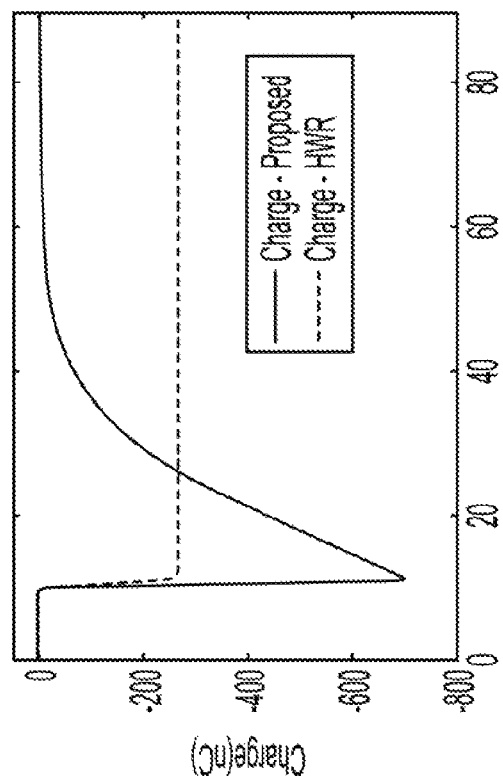
Figure 7H:
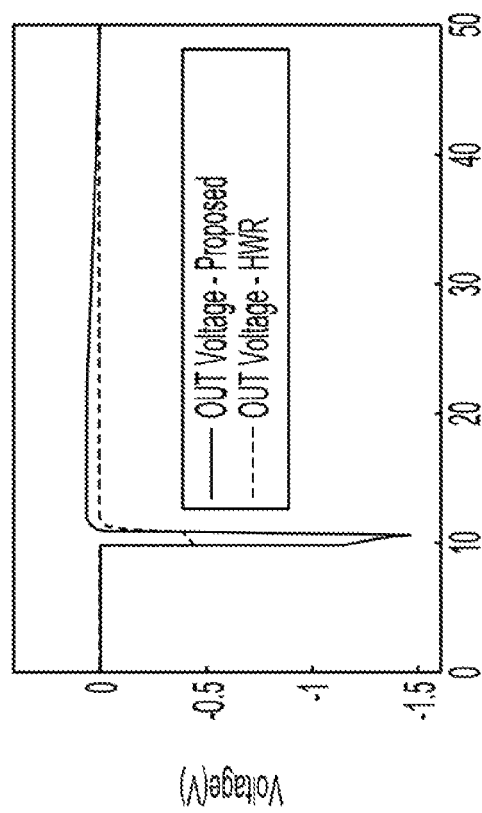
Figure 7J:
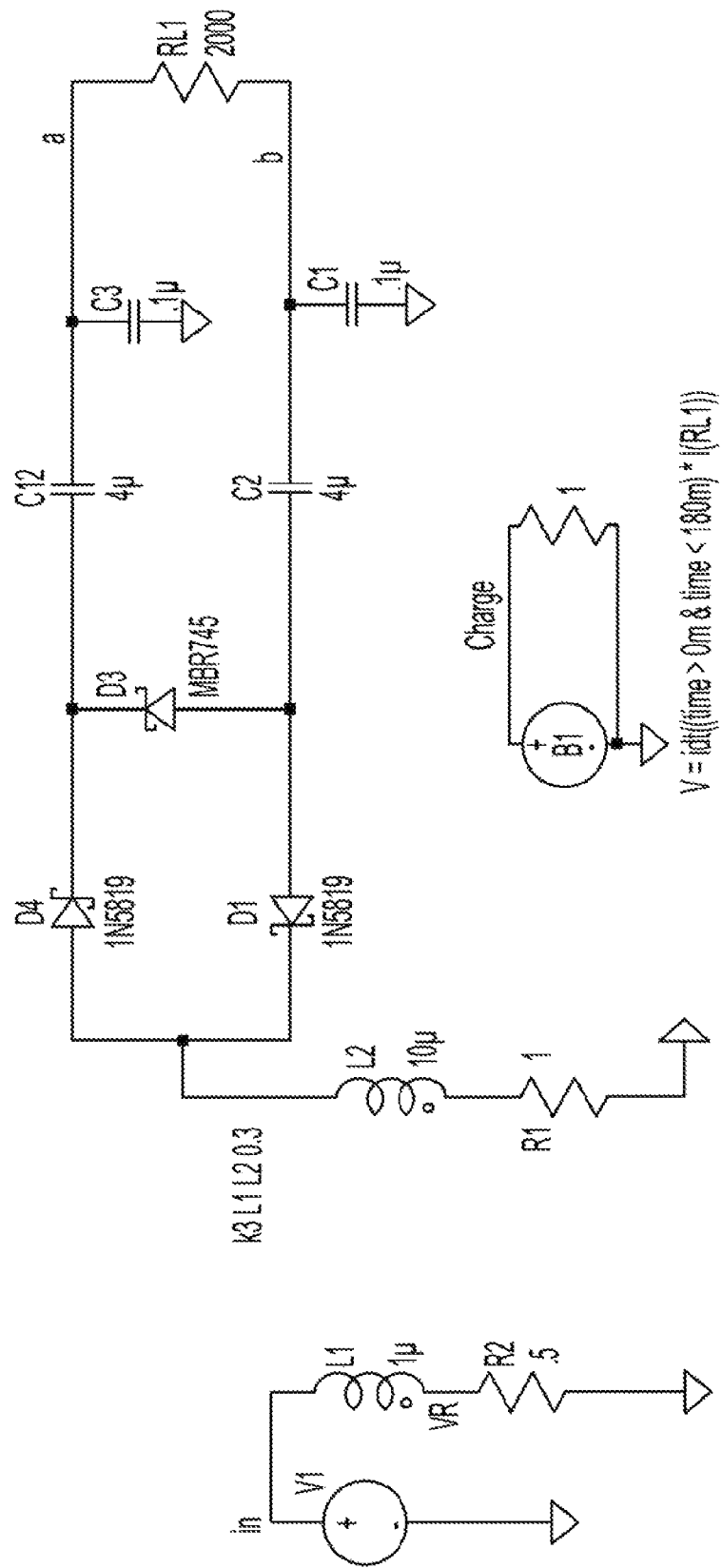
Figure 7L:
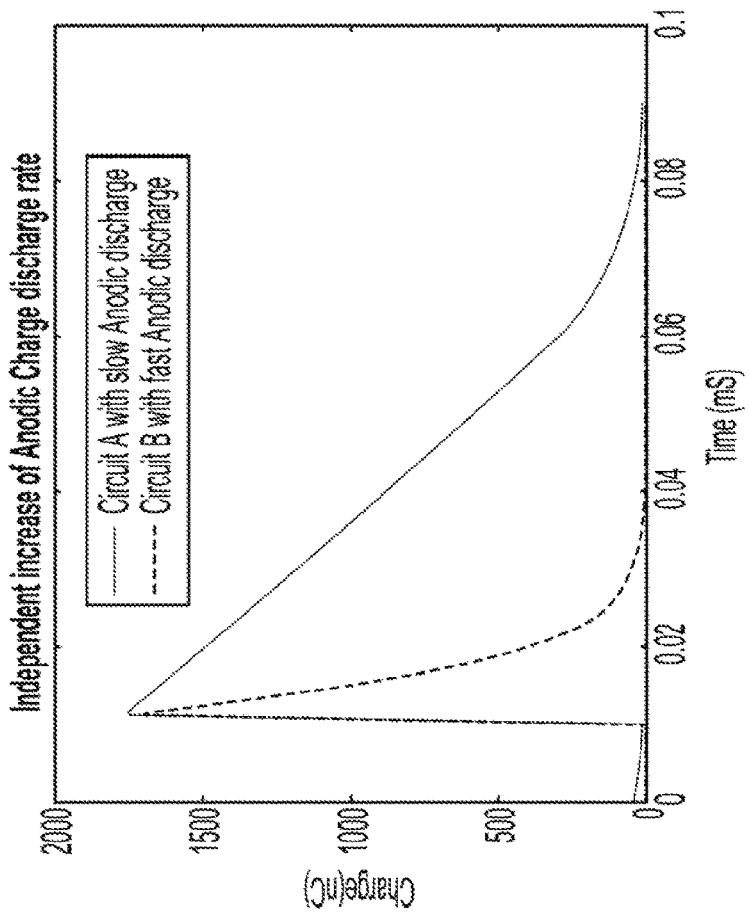
Figure 7K:
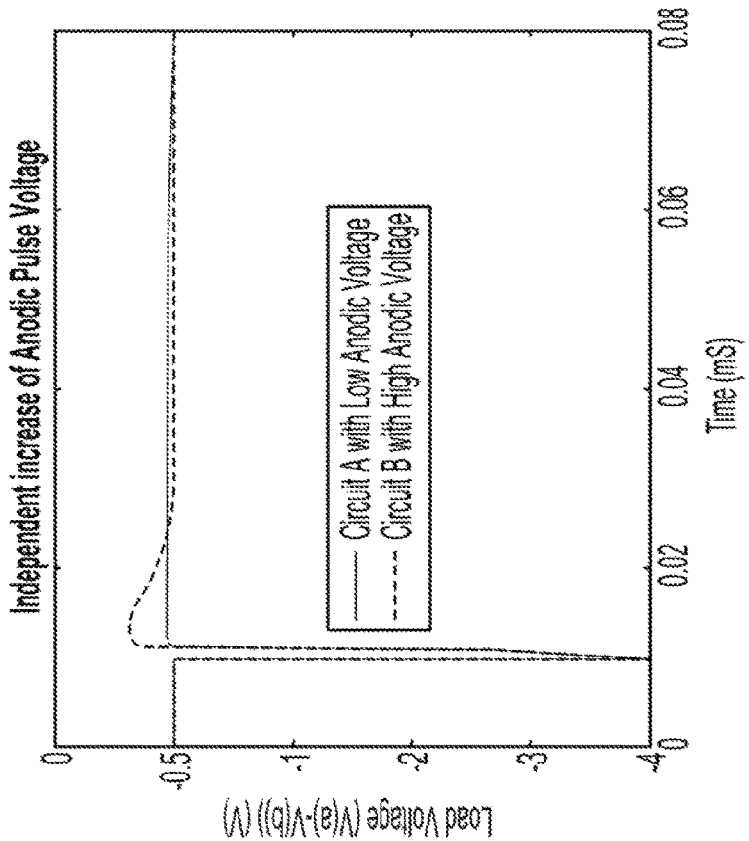

The circuit 700 may be further modified by adding a diode D3 as shown in FIG. 7J to increase the anodic voltage without affecting the cathodic voltage. The effect of the modified circuit on the load voltage and charge is shown in FIGS. 7K and 7L. Circuit A referenced in FIGS. 7K and 7L is the circuit of FIG. 7J without diode D3, and Circuit B referenced in FIGS. 7K and 7L is the circuit of FIG. 7J. This modification also helps to control the anodic charge decay rate independently from the cathodic charge decay rate. This is useful when tuning the shape of the stimulating waveform without affecting the efficiency of the system. It is not possible to independently tune the anodic decay rates is in existing half wave rectifiers and voltage doubling circuits, which are monophasic.

Larger values of capacitance for $C_{s1}$ and $C_{s2}$ compared to $C_{L1}$ and $C_{L2}$ may be chosen. Larger values of the series capacitance may lead to higher load current and load voltage. This provides less resistance to current flow through the diodes. Also, this leads to quick charging and discharging of the cathodic pulse.

The output voltage for a Type 3 RF voltage input, coil relative polarity shown in the circuit 700, can be increased by increasing the conduction of the diode $D_2$. For example, replacing a 1N5819 diode with MBR745 diode increases the output voltage. Also, a parallel diode and capacitor to $D_2$ and $C_{s2}$ pair can increase the output voltage.

The output voltage and the charge balance waveforms of an HWR and the circuit 700 are shown below. The two systems are compared under similar input waveform, transmitter-receiver coils and loading conditions. The details of the simulation parameters are given in the table below. The output voltage of the proposed circuit is higher than the HWR. Also, unlike the HWR, the circuit 700 achieves charge balance.

|  | HWR | Circuit 700 |
| --- | --- | --- |
| Diodes used | 1N5819 | 1N5819 (MBR745) |
| Load | 2 kΩ | 2 kΩ |
| Input waveform | same | same |
| Tx coil Inductance | 1 uH, 0.5 Ω | 1 uH, 0.5 Ω |
| Rx coil Inductance | 10 uH, 1 Ω | 10 uH, 1 Ω |
| Capacitors | 0.2 uF (tried higher values) | 0.2 uF and 5 uF |

A comparison of output voltage and charge between the proposed system described herein and HWR are shown in FIGS. 7H and 7I.

Figure 8B:
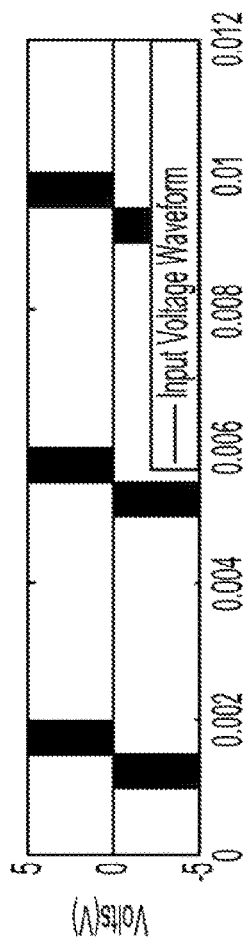
FIGS. 8A-8D illustrate a circuit schematic of the system and characteristics of these components, according to various embodiments of the invention.
Figure 8C:
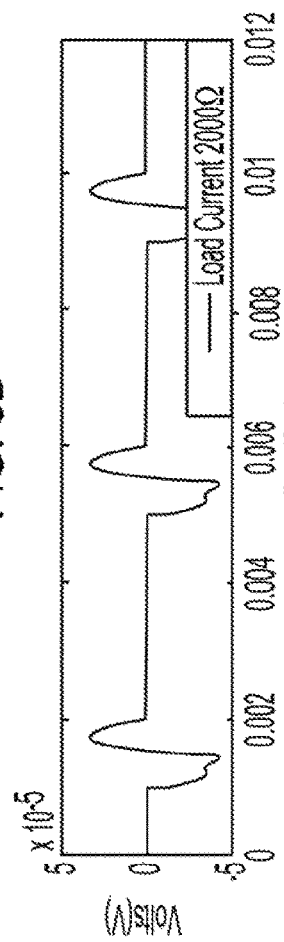
Figure 8D:
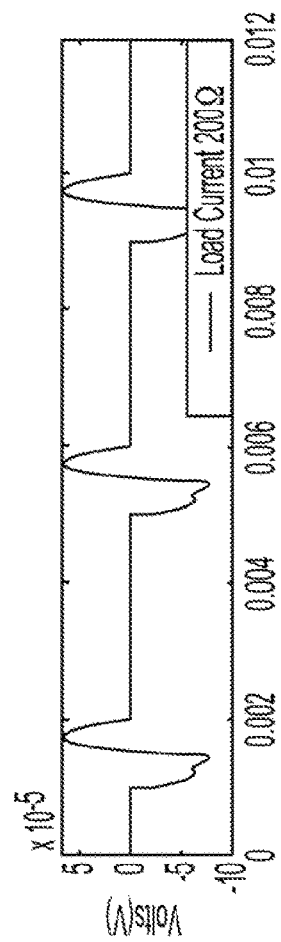
Figure 8A:
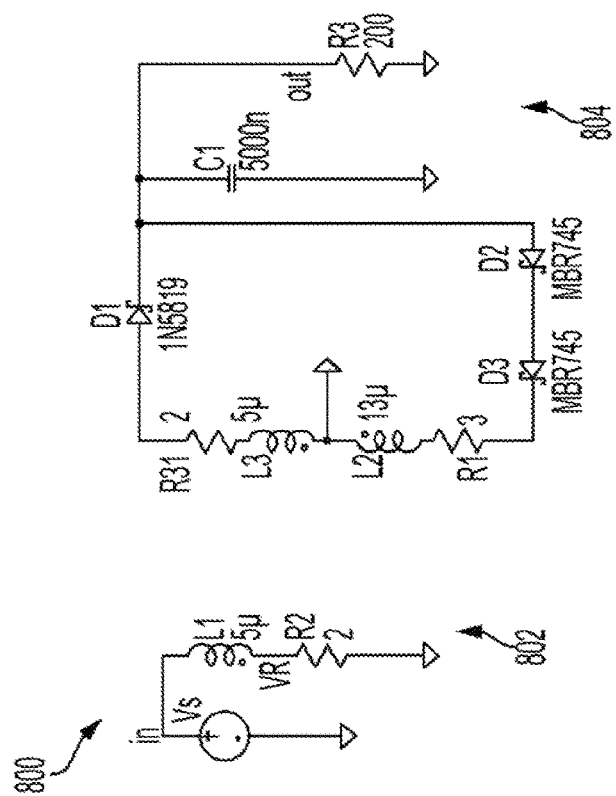

The circuit 800 shown in FIG. 8A may be used in the systems and methods described herein. The circuit 800 includes a transmitter portion 802 and a receiver portion 804. The transmitter portion 802 may be used with the external RF coils 206 and the receiver portion 804 may be used with the internal RF coils 204.

Similar to the circuit 700, the circuit 800 is charge-balanced. However, the circuit 700 results in different waveforms based on load resistance, which is the resistance from the eye. Thus, different eyes and different states of the eyes may result in different load resistances, and the shape of the waveform from the receiver portion 704 may vary based on the eye.

In contrast, the circuit 800 is load independent. That is, regardless of the load resistance from the eye of the user, the same waveform shape is achieved from the receiver portion 804. FIG. 8B illustrates the input voltage waveform. FIGS. 8C and 8D illustrate the same waveform being achieved at the receiver portion 804 regardless of the load resistance, demonstrating the ability of the circuit 800 to be load independent.

Figures 9A, 9B:
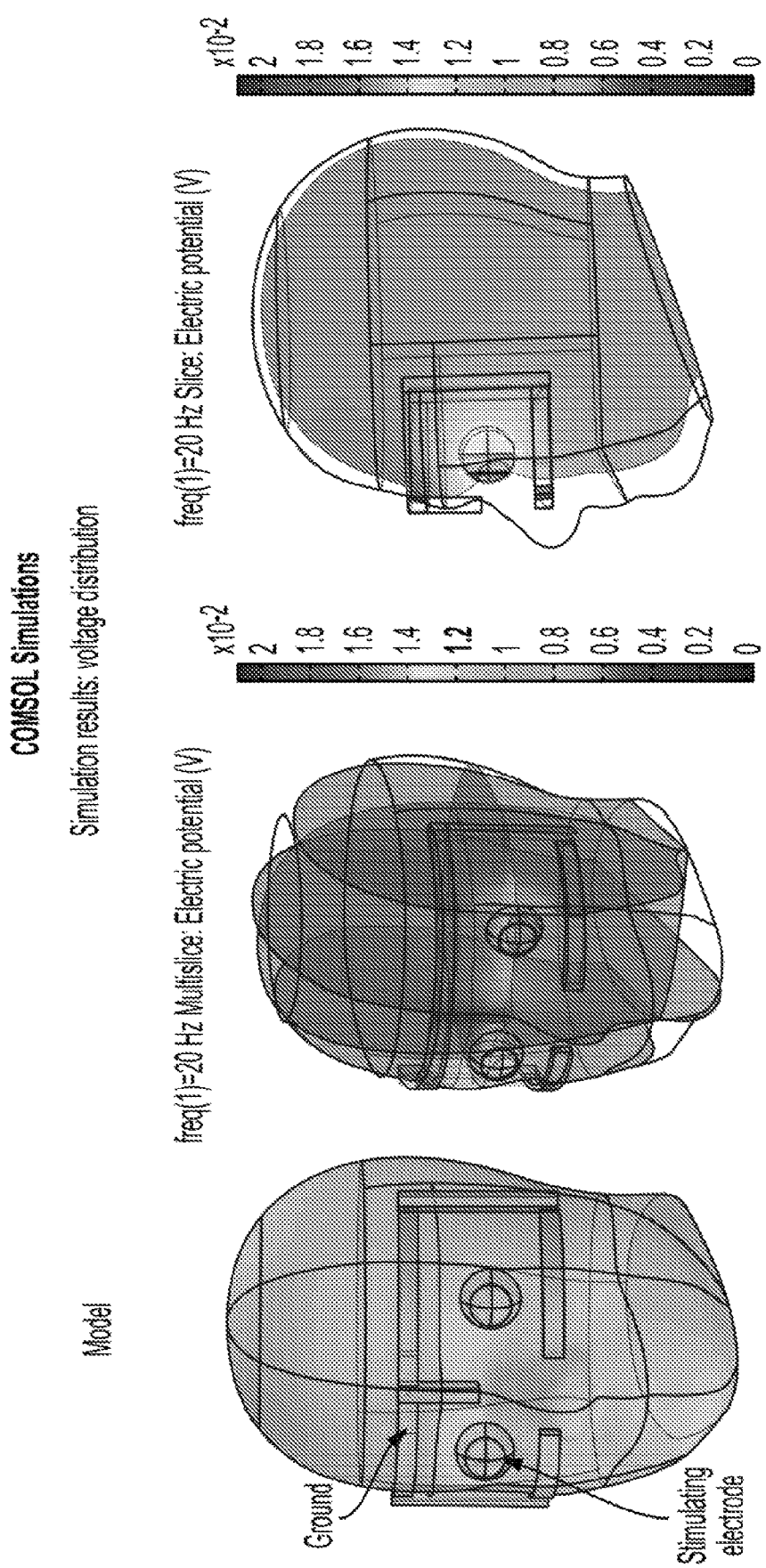
FIGS. 9A-9B illustrate a simulation of the system, according to various embodiments of the invention.

Shifting focus back to the effects of electrical stimulation, neurons communicate via electrical signals and electrical stimulation has shown to induce neural plasticity and protection of the damaged nervous system, including that of the retina. While electrical stimulation of the eye has shown to be effective, it is important to avoid stimulation of other neurons including those in the central nervous system. Therefore, a ground system configuration was designed that can substantially limit the voltage distributions as well as the induced electric fields in the brain using COMSOL Multiphysics software. FIG. 9A shows a human head model including the designed ground system and stimulating electrodes. The focalized voltage distributions into the eyes are depicted in FIG. 9B. The initial simulation findings demonstrate the potential for select stimulation of the eye and further enhancing the voltage gradient along the retina. This shows the greatest efficacy for stimulation of the retina as well as avoiding induced neural activities in other parts of the human body using the designed ground geometry.

Preliminary computational results show that, with a 12 turn coil of inductance 5 uH on the e-lens sized for a rat's eye (approximately 8 mm diameter), the retina can be stimulated with an AC current of approximately 100 uA using an external coil powered through a 1 A current, which is comparable to current magnitudes used for currently commercialized artificial retina systems and demonstrated to be safe at extremely low frequencies. To further improve the coupling between external coil and lens coil, solutions can be used that are directly applicable to the proposed geometry. In some embodiments, the wireless lens is to be worn for a limited period daily—primarily at night—with the transmitting external coil integrated on a wearable mask or similar device.

Chromatin is a compact and highly organized hierarchical assembly of DNA and proteins that is intricately folded into three dimensions, forming different levels of organization in the nucleus. Chromatin packing density has a non-monotonic effect on the probability of gene expression, enhancing the rates of expression at chromatin packing densities below −35% of chromatin volume concentration and suppressing expression at higher chromatin densities due to the competing effects of two consequences of molecular crowding, increased binding of transcriptional complexes and suppressed diffusion. Recent evidence indicates that chromatin packing scaling modulates both transcriptional diversity (the dynamic range of gene expression) and intercellular variation in gene transcription. Chromatin packing regulates cells' transcriptional access to their genomic space and is expected to have implications on a wide range of cellular processes (e.g., cell differentiation, plasticity, tissue regeneration, and many diseases including neurodegenerative diseases). Depending on its location in the genome, DNA methylation can also impact proximal chromatin structure and regulate gene expression, playing critical roles in biological processes including embryonic development, Xchromosome inactivation, genomic imprinting, and chromosome stability. Hence, determining the methylation status at a single base resolution in the genome is an important step in elucidating its role in regulating many cellular processes and its disruption in disease states.

To begin to explore the extent to which DNA methylation changes can be altered in response to in vivo electrical stimulation, whole genome bisulfite sequencing (WGBS) on 3 TES-treated and 3 sham-treated retinal degeneration (RCS) rat retinas was performed. WGBS enables the detection of DNA methylation at single base-pair resolution. The treatment of DNA with sodium bisulfite allows the discrimination of methylated and unmethylated cytosines in a CpG dinucleotide. Comparative epigenomics have revealed that genome-wide patterns of DNA methylation for certain genomic elements are conserved across vertebrates, suggesting that the regulatory roles of DNA methylation are also conserved across species. Briefly, genomic DNA is sheared, end-repaired, 3'-adenylated, and ligated to adaptors. The adapter-ligated DNA is then treated with sodium bisulfite and PCR amplified to reach the yield needed for sequencing. Paired end sequencing of bisulfite-converted libraries was performed on the NovaSeq 6000 system. WGBS reads were aligned to the *Rattus norvegicus* RNOR6 genome assembly using open source Bismark Bisulfite Read Mapper with the Bowtie2 alignment algorithm.

Figure 10:
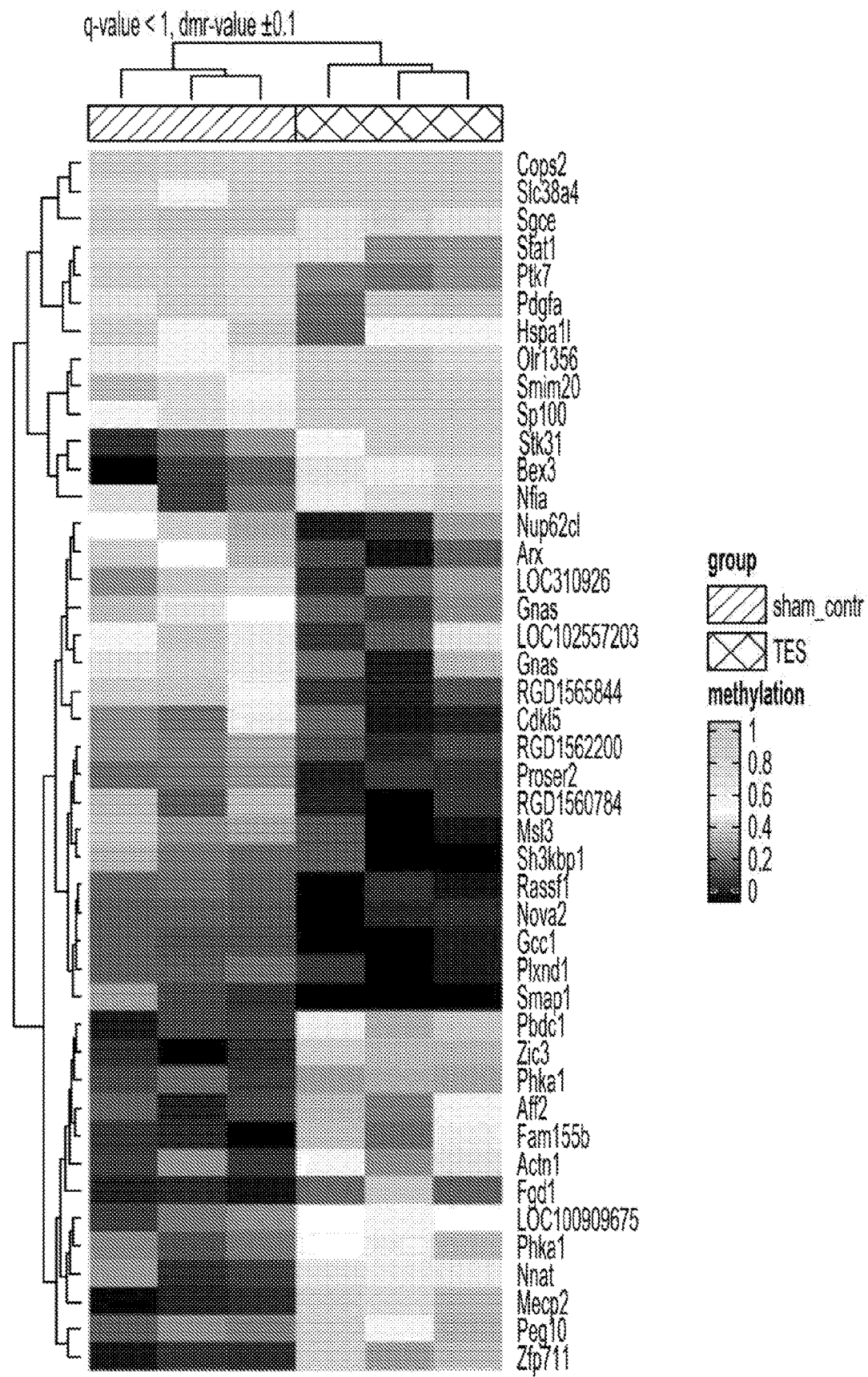
FIG. 10 illustrates a heatmap of unsupervised hierarchical clustering of the most significant differentially methylated regions (DMRs), according to various embodiments of the invention.

Data analysis conducted using the software package metilene identified 2996 statistically significant DNA methylation differences between TES and sham-treated retinas. Unsupervised hierarchical clustering of the most significant differentially methylated regions (DMRs) and associated genes precisely separated the control sham group from the electrically stimulated group (FIG. 10). To obtain a preliminary investigation of the molecular mechanisms underlying electrical stimulation, genes associated with the most significant DMRs were submitted to Ingenuity Pathway Analysis (IPA) core analysis. Of most relevance, the top enriched disease categories with a p-value less than 10-3 were implicated to neurological disorders, including many hereditary and xlinked disorders. Among the most significantly hypermethylated genes implicated to progression of neurological diseases were Kcnab2, Cnr, and Nfia (FIG. 10). Actin cytoskeleton and pdgf signaling were the top enriched canonical pathways, with cytoskeletal remodeling being important in multiple aspects of retina development and also neuronal function. In addition, hypomethylation of the pro-survival genes bdnf and pdgfa was identified, which have been previously shown to be electrically induced. Other genes within significant DMRs include hypermethylation of Retinitis Pigmentosa GTPase Regulator (rpgr) and rpgr interacting protein 1 (rpgrip1). Targeted bisulfite amplicon sequencing was performed on 18 of these DMRs to confirm DNA methylation changes in response to TES stimulation in an independent cohort of RCS rat retinas. Of these 18 DMRs, 9 showed good concordance between the whole genome and targeted bisulfate sequencing runs, with a correlation of 0.725 (FIG. 11), validating the method of identifying consistent DMRs after TES treatment.

Figure 11:
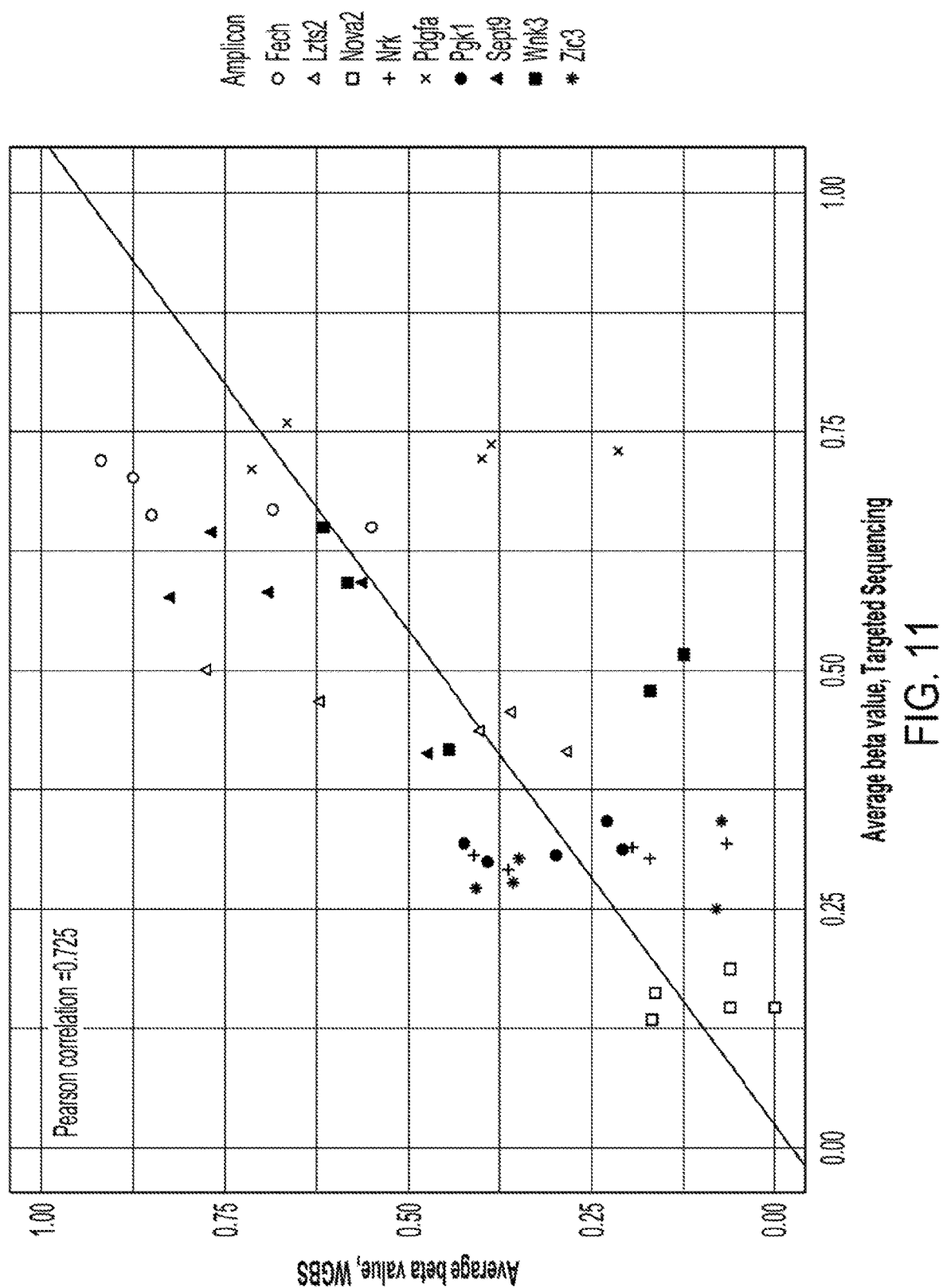
FIG. 11 illustrates a scatterplot showing the correlation between methylation beta values derived from whole genome bisulfite sequencing (WGBS) and targeted bisulfite sequencing, according to various embodiments of the invention.
Figure 12:
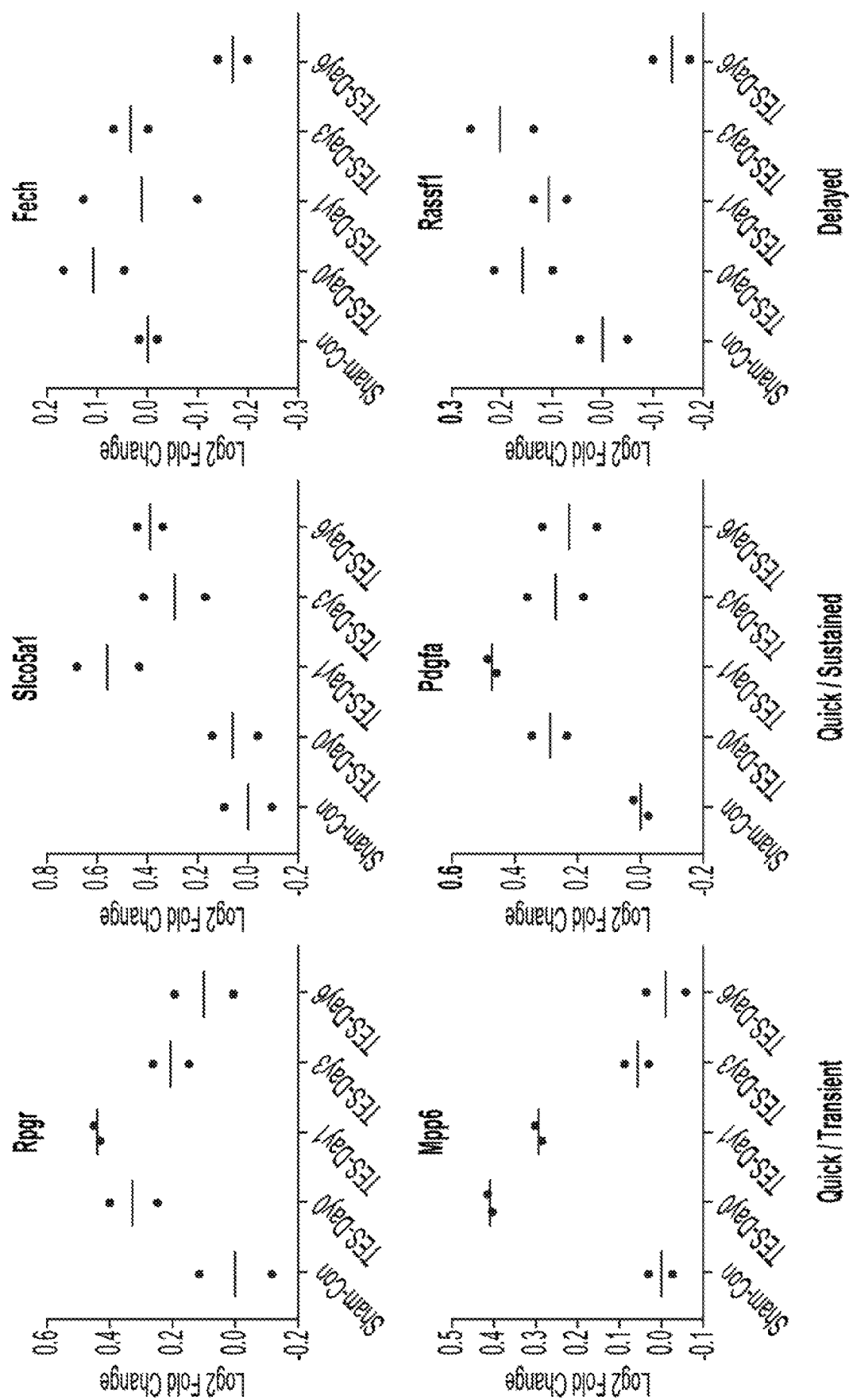
FIG. 12 illustrates expression levels of selected genes determined by quantitative reverse transcription polymerase chain reaction (qRT-PCR) of retinal degeneration rat retinas at multiple time points post transcorneal electrical stimulation (TES), according to various embodiments of the invention.

To begin to elucidate the functional consequences of the observed epigenetic deregulation and provide a more direct link of differentially methylated genes with functional changes and neuroprotection targeted gene expression by quantitative reverse transcription polymerase chain reaction (qRTPCR) on 30 genes associated with DMRs in an independent cohort of TES (n=2) and sham-stimulated (n=2) RCS rat retinas was measured. The durability of the response over time was examined, whereby rat retinas were harvested on same day, day 1, 3 and 6 post stimulation. Gene expression was normalized to an internal reference gene (Gapdh) and expression was secondarily normalized to shamstimulated controls. RNA expression of 30 genes associated with DMRs were graphed and analyzed by principle component analysis (PCA). Of 30 genes, 27 (90%) genes were either overexpressed (n=19) or downregulated (n=8) by at least 20% at any time point (FIG. 12). Three genes demonstrated no change in gene expression. PCA revealed three different expression potentials defined by timing and duration of expression change compared to sham controls. There were 12 genes that showed quick (day 0-1) induction immediately after TES treatment but expression was transient and reverted back to levels of the control by day 3-6. This included the upregulation of genes related to healthy retinal development, such as Rpgr and Ablim123, and also upregulation of genes related to cytoskeletal remodeling, such as Sept9 and Mpp6, which has also been shown to be important in retinal regeneration in zebrafish24. Another group of 7 genes showed quick and sustained induction of expression up to day 6. This group of genes included Pdgfa and Slco5a1 upregulation (FIG. 11). Pdgfa is not only known to be stimulated by electrical stimulation3, but also known to attract astrocytes, and promote cell survival. Slco5a1 is a gene with known functions in rod cell function.

The last group of 8 genes were downregulated compared to control but reduced expression was delayed and not evident until day 6 post TES. These included the downregulation of genes known to promote angiogenesis and neovascularization, such as Fgf8 and Fech (FIG. 12). Aberrant ocular neovascularization driven by angiogenic factors has been shown to be a cause of several blinding eye diseases27, and inhibition of these factors, including Fech28, are currently being explored as potential therapeutics. In addition, proapoptotic genes such as Rassf129 (FIG. 11) were also found to be downregulated. As genes associated with cell proliferation and apoptosis were identified in both the methylation and gene expression analyses, we explored the possibility that TES treatment could also inhibit the apoptosis of retinal cells. To achieve this, immunohistochemistry (IHC) staining of cleaved caspase-3, a marker for apoptotic cells, was performed on whole eye sections from TES or sham-treated rats, at multiple time points after stimulation. Three separate field of views were examined for each eye, with an average of 1353 cells counted in all layers of the retina for each eye. The percent of apoptotic cells found was 1.46% in the control rats, compared to 0.89% in the TES-treated rats at after day 6 (p-value 0.021).

Collectively, these preliminary data provide compelling evidence that TES can induce epigenetic and chromatin level changes (FIGS. 10-12). Most importantly, it is shown that these changes translate to functional changes as evidenced by corresponding gene expression changes which can directly be linked to retinal regeneration, increased cell survival and inhibition of apoptosis, cytoskeletal remodeling and inhibition of ocular neovascularization, supporting the notion that TES induces neuroepigenetic remodeling leading to the survival and regeneration of the retina. Therefore, the preliminary data points to TES triggering a host of beneficial molecular changes in the retina.

FIGS. 13A-13B illustrate differentially methylated regions (DMRs) identified as being most significantly altered after electrical stimulation, and these DMRs could serve as putative biomarkers of response. The list in FIGS. 13A-13B is not an exclusive list.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system comprising:
    an external radiofrequency (RF) coil configured to transmit RF signals toward an eye of a user, the external RF coil configured to be spaced apart from the eye of the user when transmitting the RF signals; and
    a wearable device including:
        a curved material configured to be removably disposed on the eye and having an aperture located at a center of the curved material to allow for corneal oxygenation,
        a plurality of internal RF coils located on or within the curved material and configured to receive the RF signals from the external RF coil, and
        a plurality of stimulating electrodes including a positive electrode and a negative electrode electrically connected to the plurality of internal RF coils, the positive electrode positioned on the curved material and configured to electromagnetically stimulate a retina of the eye, causing changes to cells or tissue of the eye or causing changes to cells or tissue adjacent to the eye.

2. The system of claim 1, wherein the plurality of stimulating electrodes further including a ground electrode, wherein the positive electrode is positioned on an inner surface of the curved material, and wherein the negative electrode and the ground electrode are positioned on an outer surface of the curved material or an area of the user's body near or surrounding the eye.

3. The system of claim 1, wherein the curved material includes a plurality of grooves, and each internal RF coil of the plurality of internal RF coils is configured to be located in a respective groove of the plurality of grooves.

4. The system of claim 1, wherein the internal RF coils are made of metals or other conductive materials.

5. The system of claim 1, wherein the positive electrode produces a symmetric or asymmetric charge-balanced waveform that is used to stimulate the retina of the eye or an area adjacent to the eye.

6. The system of claim 1, wherein the external RF coil is integrated into a mask or an eyeglass frame configured to be worn by the user.

7. The system of claim 1, wherein the plurality of stimulating electrodes are further configured to electromagnetically stimulate a lacrimal gland for treatment of dry eye.

8. The system of claim 1, wherein the plurality of stimulating electrodes are further configured to electromagnetically stimulate an optic nerve.

9. The system of claim 1, wherein the plurality of stimulating electrodes are further configured to electromagnetically stimulate a ciliary body.

10. The system of claim 1, wherein the positive electrode is positioned on a lesser curvature of the curved material and the negative electrode is positioned on a greater curvature of the curved material.

11. A system for transcorneal electrical stimulation, comprising:
- an external radiofrequency (RF) coil configured to transmit RF signals; and
- a wearable device configured to be removably disposed on an eye of a user, the wearable device including:
  - a curved material configured to be removably placed on the eye, the curved material having an inner surface and an outer surface, the inner surface configured to removably contact the eye, the curved material defining an aperture located at a center of the curved material to allow for corneal oxygenation,
  - a plurality of internal RF coils located within the curved material and configured to receive the RF signals from the external RF coil, and
  - a plurality of stimulating electrodes electrically connected to the plurality of internal RF coils, the plurality of stimulating electrodes including a ground electrode located on the outer surface of the curved material, a negative electrode located on the inner surface or the outer surface of the curved material, and a positive electrode located on the inner surface of the curved material and configured to electromagnetically stimulate a portion of the eye or an area adjacent to the eye, causing changes to cells or tissue of the eye or causing changes to cells or tissue adjacent to the eye.

12. The system of claim 11, wherein the plurality of stimulating electrodes include one or more capacitors and one or more diodes.

13. The system of claim 11, wherein:
the curved material includes a plurality of grooves; and
each internal RF coil of the plurality of internal RF coils is configured to be located in a respective groove of the plurality of grooves.

14. The system of claim 11, wherein the internal RF coils are made of metals or other conductive materials.

15. The system of claim 11, further comprising a circuit configured to generate or produce a symmetric or asymmetric charge-balanced waveform used to stimulate the portion of the eye or the area adjacent to the eye.

16. The system of claim 11, wherein the external RF coil is integrated into a mask or an eyeglass frame configured to be worn by the user.

17. The system of claim 11, wherein the area adjacent to the eye is a lacrimal gland for treatment of dry eye.

18. The system of claim 11, wherein the portion of the eye is a retina and/or an optic nerve.

19. The system of claim 11, wherein the portion of the eye is a ciliary body.

20. The system of claim 11, wherein the plurality of stimulating electrodes are powered by a triboelectric generator.

* * * * *